United States Patent [19]

Krueger et al.

[11] Patent Number: 5,691,034
[45] Date of Patent: Nov. 25, 1997

[54] ELASTOMERIC LAMINATES WITH MICROTEXTURED SKIN LAYERS

[76] Inventors: Dennis L. Krueger; Joseph T. Bartusiak; Thomas P. Hanschen; Karen M. Capik, all of P.O. Box 33427, St. Paul, Minn. 55133-3427

[21] Appl. No.: 442,506

[22] Filed: May 16, 1995

Related U.S. Application Data

[60] Division of Ser. No. 503,716, Mar. 30, 1990, Pat. No. 5,501,679, which is a continuation-in-part of Ser. No. 438,593, Nov. 17, 1989, abandoned.

[51] Int. Cl.$^6$ .................................................. D06N 7/04
[52] U.S. Cl. ............................................ 428/152; 428/910
[58] Field of Search ........................................ 428/152, 910

[56] References Cited

U.S. PATENT DOCUMENTS

| | | | |
|---|---|---|---|
| Re. 28,688 | 1/1976 | Cook | 260/4 |
| 3,265,765 | 8/1966 | Holden et al. | 260/876 |
| 3,365,315 | 1/1968 | Beck et al. | 106/40 |
| 3,424,649 | 1/1969 | Nyberg et al. | 161/253 |
| 3,479,425 | 11/1969 | Lefevre et al. | 264/171 |
| 3,557,265 | 1/1971 | Chisholm et al. | 264/47 |
| 3,562,356 | 2/1971 | Nyberg | 260/876 |
| 3,694,815 | 10/1972 | Burger | 2/224 A |
| 3,700,633 | 10/1972 | Wald et al. | 260/380 B |
| 3,819,401 | 6/1974 | Massengale et al. | 156/85 |
| 3,912,565 | 10/1975 | Koch et al. | 156/85 |
| 4,082,877 | 4/1978 | Shadle | 428/35 |
| 4,116,917 | 9/1978 | Eckert | 260/33.6 AQ |
| 4,143,195 | 3/1979 | Rasmussen | 428/116 |
| 4,152,287 | 5/1979 | Cloeren | 264/171 |
| 4,156,673 | 5/1979 | Eckert | 260/33.6 AQ |
| 4,181,752 | 1/1980 | Martens et al. | 427/54.1 |
| 4,303,571 | 12/1981 | Jansen et al. | 260/33.6 AQ |
| 4,337,771 | 7/1982 | Pieniak et al. | 128/287 |
| 4,386,125 | 5/1983 | Shiraki et al. | 428/36 |
| 4,476,180 | 10/1984 | Wnuk | 428/220 |
| 4,515,595 | 5/1985 | Kievit et al. | 604/385 A |
| 4,524,099 | 6/1985 | Di Luccio | 428/213 |
| 4,552,795 | 11/1985 | Hansen et al. | 428/110 |
| 4,563,185 | 1/1986 | Reiter | 604/385 A |
| 4,681,580 | 7/1987 | Reising et al. | 604/385 A |
| 4,710,189 | 12/1987 | Lash | 604/385 A |
| 4,767,726 | 8/1988 | Marshall | 501/33 |
| 4,795,456 | 1/1989 | Borgers et al. | 604/390 |
| 4,813,946 | 3/1989 | Sabee | 604/385.2 |
| 4,813,947 | 3/1989 | Korpman | 604/387 |
| 4,820,590 | 4/1989 | Hodgson, Jr. et al. | 428/516 |
| 4,834,741 | 5/1989 | Sabee | 604/385.2 |
| 4,857,409 | 8/1989 | Hazelton et al. | 428/494 |
| 4,880,682 | 11/1989 | Hazelton et al. | 428/152 |
| 5,156,789 | 10/1992 | Amaral et al. | 264/160 |
| 5,344,691 | 9/1994 | Hanschen et al. | 428/152 |
| 5,354,597 | 10/1994 | Capik et al. | 428/152 |
| 5,376,430 | 12/1994 | Swenson et al. | 428/152 |
| 5,422,178 | 6/1995 | Swenson et al. | 428/343 |
| 5,424,025 | 6/1995 | Hanschen et al. | 264/288.8 |
| 5,429,856 | 7/1995 | Krueger et al. | 604/370 |
| 5,462,708 | 10/1995 | Swenson et al. | 264/174.11 |
| 5,468,428 | 11/1995 | Hanschen et al. | 264/483 |
| 5,501,679 | 3/1996 | Krueger et al. | 604/393 |

FOREIGN PATENT DOCUMENTS

| | | |
|---|---|---|
| 0 119 827 A2 | 9/1984 | European Pat. Off. |
| 1264196 | 2/1972 | United Kingdom |
| 2160473 | 12/1985 | United Kingdom |
| 2173688 | 10/1986 | United Kingdom |
| 2190406 | 11/1987 | United Kingdom |

*Primary Examiner*—James J. Bell
*Attorney, Agent, or Firm*—Gary L. Griswold; Walter N. Kirn; William J. Bond

[57] ABSTRACT

Microtextured elastomeric laminates comprising at least one elastomeric layer and at least one thin skin layer is preferably prepared by coextrusion of the layers followed by stretching the laminate past the elastic limit of the skin layers and then allowing the laminate to recover.

14 Claims, 14 Drawing Sheets

5,691,034

ELASTOMERIC LAMINATES WITH MICROTEXTURED SKIN LAYERS

This is a division of application Ser. No. 07/503,716 filed Mar. 30, 1990 now U.S. Pat. No. 5,501,679, which is a continuation-in-part of U.S. application Ser. No. 07/438,593, filed Nov. 17, 1989 now abandoned.

FIELD OF THE INVENTION

The invention concerns elastomeric films and more specifically concerns laminates. These laminates are particularly useful in garment applications.

BACKGROUND

Elastomeric films have for some time been used and discussed in the literature with regard to their applications in disposable products, such as baby diapers and adult incontinent devices. These elastomeric webs or films are used primarily in the body hugging portions of garments. In diapers, for example, elastomeric bands are typically used in the waistband portions such as discussed in U.S. Pat. No. 4,681,580, issued to Reising et al., and Lash, U.S. Pat. No. 4,710,189. Both these patents describe the use of elastomeric materials which have a heat stable and a heat unstable form. The heat unstable form is created by stretching the material when heated around its crystalline or second phase transition temperature followed by a rapid quenching to freeze in the heat unstable extended form. The heat unstable elastomeric film can then be applied to the, e.g., diaper and then heated to its heat stable elastomeric form. This will then result in a desirable shirring or gathering of the waistband of the diaper. A problem with these materials, other than cost, is the fact that the temperature at which the material must be heated to release the heat unstable form is an inherent and essentially unalterable property of the material to be used. This extreme inflexibility can cause severe problems. First, it is more difficult to engineer the other materials with which the waistband is associated so that they are compatible with the temperature to which the elastomeric member must be heated in order to release the heat unstable form. Frequently this temperature is rather high which can potentially cause significant problems with the adhesive used to attach the elastomeric waistband, or, e.g., the protective back sheet or top sheet of the diaper. Further, once chosen the elastomer choice can constrain the manufacturing process rendering it inflexible to lot variations, market availability and costs of raw materials (particularly elastomer(s)), customer demands, etc.

Elastomers discussed in the above two patents, suitable for use in diapers, include those described in more detail by Massengale et al., U.S. Pat. No. 3,819,401, Koch et al., U.S. Pat. No. 3,912,565, Cook U.S. Pat. RE 28,688 and commercial materials, which are believed to correspond to those described in Hodgson et al., U.S. Pat. No. 4,820,590 issued to Exxon Chemical Patents Inc. Massengale et al. describes an elastomeric member which can be used to shirr flexible articles such as diapers, in the waistband and leg portions. The polymers described are polyvinyl chlorides containing one or more specific plasticizers. The polymers specifically described required heating to a temperature of 100° C. in order to cause the tape to shrink to its heat stable elastomeric form. The polyvinyl chloride heat shrinkable elastomer was a proposed solution to the problems associated with attaching a conventional rubber or elastic material to a shirred article, which was required to be held in a stretched condition for it to be attached to the shirrable sheet or an even more problematic attachment to the sheet in the shirred condition.

Koch et al. describes a polyurethane heat shrinkable elastomeric material which can be used to shirr the waistband and leg portions of a diaper. The polyurethane was described as conventional heat shrinkable polyurethanes and again had to be heated to 100° C. to release the elastomeric tape to its heat stable contracted form.

An allegedly novel composition was proposed by Hodgson et al. whose elastomer is a blend of three components including predominately an ethylene copolymer elastomer modified by olefinic elastomer and process oil. A heat unstable form was again created by heating and stretching the materials, at a temperature of preferably not more than 10° F. below the crystalline melting point of the ethylene copolymer components of the composition. The material was then cooled, freezing in the heat unstable form. The stretched unstable material was then activated or relaxed at approximately the temperature at which the film was stretched. Although this material resumed its heat stable form at a lower temperature than the materials described in the above two patents, this temperature is still determined at the molecular level and is not subject to significant modification once the elastomeric material of choice is selected.

Other materials and methods have been proposed, for example Berger, U.S. Pat. No. 3,694,815, proposed a method for attaching a stretched relaxed elastic ribbon to a garment by stretching conventional elastic ribbons and immediately freezing the elastomeric material at relatively extreme low temperatures (e.g., well below ambient). This process would obviously severely constrain the processing conditions and materials which could be used when attaching the elastomeric strand to its backing. UK Pat. Application 2190406 A proposed maintaining a conventional elastomer in a stretched condition, while attaching to the member to be shirred (e.g., a diaper), by a rigidifying member, which would then be removed or destroyed following the attachment procedure. As described, the elastomers are first stretched then applied to the rigidifying member in its stretched form. Finally, Matray et al., UK Pat. 2,160,473 proposes an elastomer which will shrink at an elevated temperature (e.g. at or above 175° F. or 79.4° C.). The allegedly novel feature of this material, compared to the heat shrink materials discussed above, is that it does not require preheating during the stretching operation but rather could be stretched at ambient temperatures by a differential speed roll process or by "cold rolling". The polymer proposed was a copolymer having alternating segments of polyamidepolyether block polymers, commercially available under the trade name Pebax, particularly Pebax Extrusion grades 2533 and 3533. As an alternative this patent application proposed placing a thin EVA (ethylene-vinyl acetate) layer(s) over the elastomer by, e.g., coextrusion. The skin layer is chosen to prevent blocking or to be compatible with a later applied adhesive. It was noted that this layer can also produce a pleasing hand but so as not to interfere with heat shrinkability.

Problems with these elastomeric films include the difficulties inherent fn applying a stretched elastic member to a flexible substrate such as a disposable diaper. Although some of the elastomers proposed have the advantage that they can be applied at ambient conditions in a heat stretched unstable form, subsequent often extreme heating is required to release the heat unstable form to a contracted heat stable form. The temperature of this heat release is generally inflexible as it is determined at the molecular level of the elastomer. As such the other materials applied to the elastomer, and the process conditions at which the elastomer is used, must be carefully selected to be compatible with this heating step.

Elastomers also exhibit relatively inflexible stress/strain characteristics which cannot be chosen independently of the activation temperature. Materials with a high modulus of elasticity are uncomfortable for the wearer. Problems with a relatively stiff or high modulus of elasticity material can be exaggerated by the coefficient of friction and necking of the elastomer which can cause the material to bite or grab the wearer.

SUMMARY OF THE INVENTION

The present invention relates to non-tacky, microtextured, multi-layer elastomeric laminates. The laminates of the present invention are comprised both of an elastomeric polymeric core layer(s), which provides elastomeric properties to the laminate and one or more polymeric skin layers which are capable of becoming microtextured. This microtexturing increases the comfort level of the elastomeric material which is complemented by a significant lowering of the laminate's coefficient of friction and modulus. In preferred embodiments of the present invention the skin layer further can function to permit controlled release or recovery of the stretched elastomer, modify the modulus of elasticity of the elastomeric laminate and/or stabilize the shape of the elastomeric laminate (i.e. by controlling further necking). The laminates can be prepared by coextrusion of the selected polymers or by application of one or more elastomer layers onto one or more already formed skin layer(s). Coextrusion is preferred. The novel non-tacky microtextured laminate is obtained by stretching the laminate past the elastic limit of the outer skin layers. The laminate then recovers, which can be instantaneous, over an extended time period, which is skin layer controllable, or by the application of heat, which is also skin layer controllable.

Stretching of the laminate can be uniaxial, sequentially biaxial, or simultaneously biaxial. It has been found that the method and degree of stretch allows significant control over the microtextured surface that results, allowing formation of novel surfaces. The invention thus further provides various novel surfaces and also a method for the controlled production of these surfaces.

DETAILED DESCRIPTION OF PREFERRED EMBODIMENTS OF THE INVENTION

Figure 1:
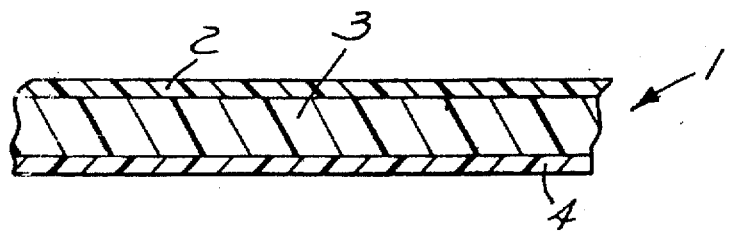
FIG. 1 is a cross-sectional segment of an extruded laminate 1 of the invention before microstructuring.

The present invention relates broadly to novel non-tacky, multi-layer elastomeric laminates comprising at least one elastomeric layer and at least one relatively nonelastomeric skin layer. The skin layer is stretched beyond its elastic limit and is relaxed with the core so as to form a microstructured surface. Microstructure means that the surface contains peak and valley irregularities or folds which are large enough to be perceived by the unaided human eye as causing increased opacity over the opacity of the laminate before microstructuring, and which irregularities are small enough to be perceived as smooth or soft to human skin. Magnification of the irregularities is required to see the details of the microstructured texture.

The elastomer can broadly include any material which is capable of being formed into a thin film layer and exhibits elastomeric properties at ambient conditions. Elastomeric means that the material will substantially resume its original shape after being stretched. Further, preferably, the elastomer will sustain only small permanent set following deformation and relaxation which set is preferably less than 20 percent and more preferably less than 10 percent of the original length at moderate elongation, e.g., about 400–500%. Generally any elastomer is acceptable which is capable of being stretched to a degree that causes relatively consistent permanent deformation in a relatively inelastic skin layer. This can be as low as 50% elongation. Preferably, the elastomer is capable of undergoing up to 300 to 1200% elongation at room temperature, and most preferably up to 600 to 800% elongation at room temperature. The elastomer can be both pure elastomers and blends with an elastomeric phase or content that will still exhibit substantial elastomeric properties at room temperature.

As discussed above, heat-shrinkable elastics have received considerable attention due to the ability to fabricate a product using the unstable stretched elastomer at ambient conditions and then later applying heat to shirr the product. Although these elastomers are contemplated for use in the present invention, other non-heat shrinkable elastomers can be used while retaining the advantages of heat shrinkability with the added dimension of the possibility of substantially controlling the heat shrink process. Non-heat shrinkable means that the elastomer, when stretched, will substantially recover sustaining only a small permanent set as discussed above. Therefore, the elastomeric layer can be formed from non-heat-shrinkable polymers such as block copolymers which are elastomeric, such as those known to those skilled in the art as A-B or A-B-A block copolymers. Such copolymers are described, for example, in U.S. Pat. Nos. 3,265,765; 3,562,356; 3,700,633; 4,116,917 and 4,156,673, the substance of which is incorporated herein by reference. Styrene/isoprene, butadiene, or ethylene-butylene/styrene (SIS, SBS, or SEBS) block copolymers are particularly useful. Other useful elastomeric compositions can include elastomeric polyurethanes, ethylene copolymers such as ethylene vinyl acetates, ethylene/propylene copolymer elastomers or ethylene/propylene/diene terpolymer elastomers. Blends of these elastomers with each other or with modifying non-elastomers are also contemplated. For example, up to 50 weight percent, but preferably less than 30 weight percent, of polymers can be added as stiffening aids such as polyvinylstyrenes, polystyrenes such as poly(alpha-methyl) styrene, polyesters, epoxies, polyolefins, e.g., polyethylene or certain ethylene/vinyl acetates, preferably those of higher molecular weight, or coumarone-indene resin. The ability to use these types of elastomers and blends provides the invention laminate with significant flexibility.

Viscosity reducing polymers and plasticizers can also be blended with the elastomers such as low molecular weight polyethylene and polypropylene polymers and copolymers, or tackifying resins such as Wingtack™, aliphatic hydrocarbon tackifiers available from Goodyear Chemical Company. Tackifiers can also be used to increase the adhesiveness of an elastomeric layer to a skin layer. Examples of tackifiers include aliphatic or aromatic liquid tackifiers, polyterpene resin tackifiers, and hydrogenated tackifying resins. Aliphatic hydrocarbon resins are preferred.

Additives such as dyes, pigments, antioxidants, antistatic agents, bonding aids, antiblocking agents, slip agents, heat stabilizers, photostabilizers, foaming agents, glass bubbles, starch and metal salts for degradability or microfibers can also be used in the elastomeric core layer(s). Suitable antistatic aids include ethoxylated amines or quaternary amines such as those described, for example, in U.S. Pat. No. 4,386,125 (Shiraki), who also describes suitable antiblocking agents, slip agents and lubricants. Softening agents, tackifiers or lubricants are described, for example, in U.S. Pat. No. 4,813,947 (Korpman) and include coumarone-indene resins, terpene resins, hydrocarbon resins and the like. These agents can also function as viscosity reducing aids. Conventional heat stabilizers include organic phosphates, trihydroxy butyrophenone or zinc salts of alkyl dithiocarbonate. Suitable antioxidants include hindered phenolic compounds and amines possibly with thiodipropionic acid or aromatic phosphates or tertiary butyl cresol, see also U.S. Pat. No. 4,476,180 (Wnuk) for suitable additives and percentages.

Short fibers or microfibers can be used to reinforce the elastomeric layer for certain applications. These fibers are well known and include polymeric fibers, mineral wool, glass fibers, carbon fibers, silicate fibers and the like. Further, certain particles can be used, including carbon and pigments.

Glass bubbles or foaming agents are used to lower the density of the elastomeric layer and can be used to reduce cost by decreasing the elastomer content required. These agents can also be used to increase the bulk of the elastomer. Suitable glass bubbles are described in U.S. Pat. Nos. 4,767,726 and 3,365,315. Foaming agents used to generate bubbles in the elastomer include azodicarbonamides. Fillers can also be used to some extent to reduce costs. Fillers, which can also function as antiblocking agents, include titanium dioxide and calcium carbonate.

Figure 22:
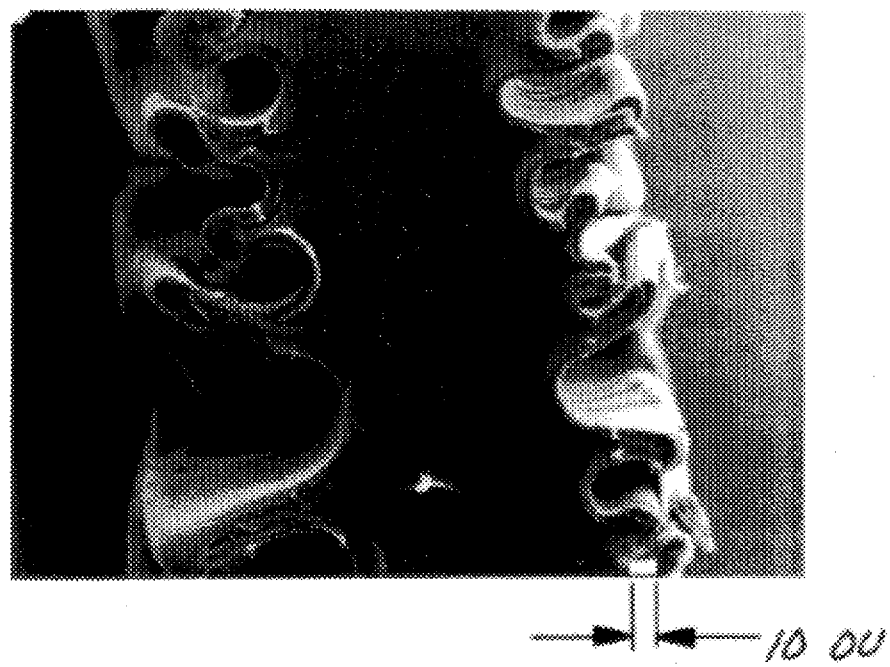
FIG. 22 is a scanning electron micrograph (400×) of a uniaxially stretched laminate with intermittent skin/core contact.
Figure 23:
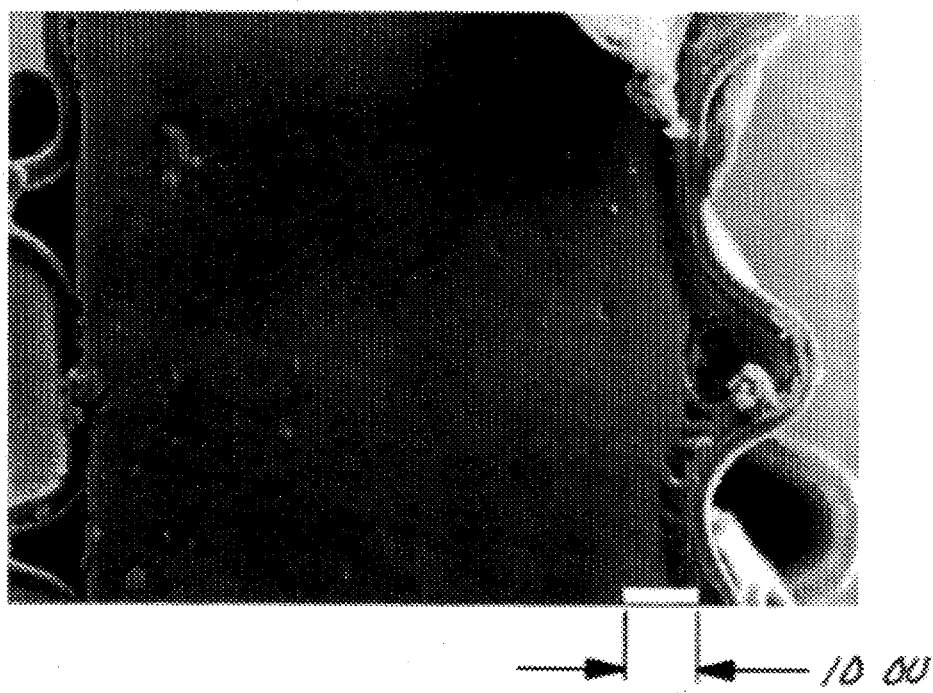
FIG. 23 is a scanning electron micrograph (1000×) of a uniaxially stretched laminate with cohesive failure of the elastomer under the folds.
Figure 24:
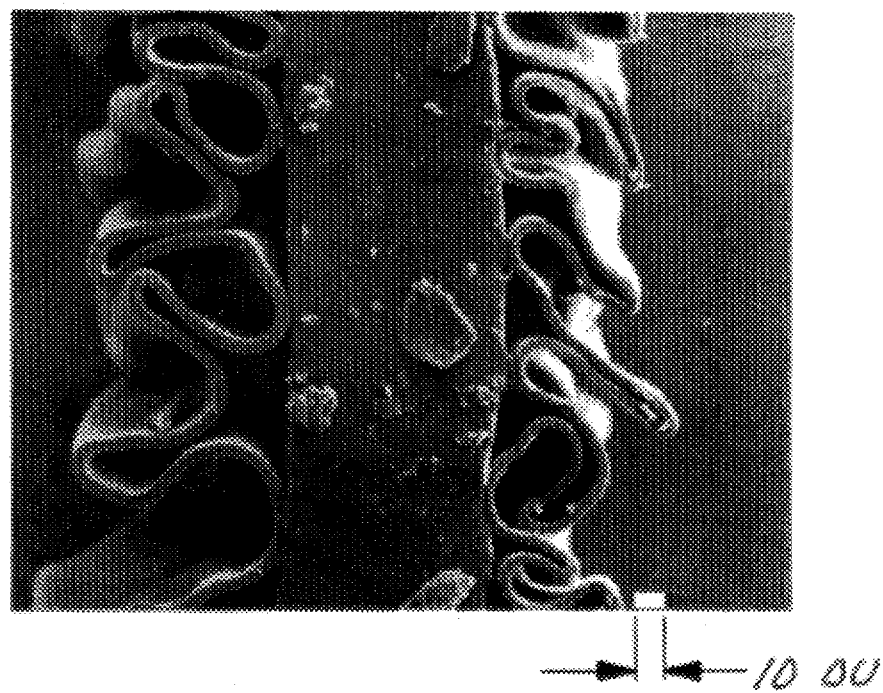
FIG. 24 is a scanning electron micrograph (400×) of a uniaxially stretched laminate with continuous skin core contact and no cohesive failure.

The skin layer can be formed of any semi-crystalline or amorphous polymer that is less elastic than the core layer(s) and will undergo permanent deformation at the stretch percentage that the elastomeric laminate will undergo. Therefore, slightly elastic compounds, such as some olefinic elastomers, e.g. ethylene-propylene elastomers or ethylene-propylene-diene terpolymer elastomers or ethylenic copolymers, e.g., ethylene vinyl acetate, can be used as skin layers, either alone or in blends. However, the skin layer is generally a polyolefin such as polyethylene, polypropylene, polybutylene or a polyethylene-polypropylene copolymer, but may also be wholly or partly polyamide such as nylon, polyester such as polyethylene terephthalate, polyvinylidene fluoride, polyacrylate such as poly(methyl methacrylate) (only in blends) and the like, and blends thereof. The skin layer material can be influenced by the type of elastomer selected. If the elastomeric layer is in direct contact with the skin layer the skin layer should have sufficient adhesion to the elastomeric core layer such that it will not readily delaminate. Acceptable skin-to-core contact has been found to follow three modes: first, full contact between the core and microtextured skin (FIG. 24); second, cohesive failure of the core under the microtexture folds (FIG. 23); and third, adhesive failure of the skin to the core under the microtexture folds with intermittent skin/core contact at the fold valleys (FIG. 22). However, where a high modulus elastomeric layer is used with a softer polymer skin layer attachment may be acceptable yet a microtextured surface may not form.

The skin layer is used in conjunction with an elastomeric layer and can either be an outer layer or an inner layer (e.g., sandwiched between two elastomeric layers). Used as either an outer or inner layer the skin layer will modify the elastic properties of the elastomeric laminate.

Additives useful in the skin layer include, but are not limited to, mineral oil extenders, antistatic agents, pigments, dyes, antiblocking agents, provided in amounts less than about 15%, starch and metal salts for degradability and stabilizers such as those described for the elastomeric core layer.

Other layers may be added between the core layer and the outer layers, such as tie layers to improve the bonding of the layers. Tie layers can be formed of, or compounded with, typical compounds for this use including maleic anhydride modified elastomers, ethyl vinyl acetates and olefins, polyacrylic imides, butyl acrylates, peroxides such as peroxypolymers, e.g., peroxyolefins, silanes, e.g., epoxysilanes, reactive polystyrenes, chlorinated polyethylene, acrylic acid modified polyolefins and ethyl vinyl acetates with acetate and anhydride functional groups and the like, which can also be used in blends or as compatiblizers in one or more of the skin or core layers. The layers are particularly useful when the bonding force between the skin and core is low. This is often the case with polyethylene skin as its low surface tension resists adhesion. However, any added layers must not significantly affect the microstructuring of the skin layers.

One unique feature of the invention is the ability to control the shrink recovery mechanism of the laminate depending on the conditions of film formation, the nature of the elastomeric layer, the nature of the skin layer, the manner in which the laminate film is stretched and the relative thicknesses of the elastomeric and skin layer(s). By controlling these variables in accordance with the teaching of this invention, the laminate film can be designed to instantaneously recover, recover over time or recover upon heat activation.

A laminate capable of instantaneous shrink is one in which the stretched elastomeric laminate will recover more than 15% in 1 sec. A laminate capable of time shrink is one where the 15% recovery point takes place more than 1 sec., preferably more than 5 sec., most preferably more than 20 sec. after stretch, and a laminate capable of heat shrink is where less than 15% shrink recovery occurs to the laminate in the first 20 seconds after stretch. Percent recovery is the percent that the amount of shrinkage is of the stretched length minus the original length. For heat shrink, there will be an activation temperature which will initiate significant heat activated recovery. The activation temperature used for heat shrink will generally be the temperature that will yield 50% of the total possible recovery ($T_{a-50}$) and preferably this temperature is defined as the temperature which will yield 90% ($T_{a-90}$) of the total possible recovery. Total possible recovery includes the amount of preactivation shrinkage.

Generally, where the skin layer of the laminate is relatively thin, the laminate will tend to contract or recover immediately. When the skin thickness is increased sufficiently, the laminate can become heat shrinkable. This phenomenon can occur even when the elastomeric layer is formed from a non-heat shrinkable material. Further, by careful selection of the thicknesses of the elastomeric layer and the skin layer(s) the temperature at which the laminate recovers by a set amount can be controlled within a set range. This is termed skin controlled recovery where generally by altering the thickness or composition of the skin one can raise the activation temperature of an elastomeric core by a significant degree, generally more than at least 10° F. (5.6° C.) and preferably by 15° F. (8.3° C.) and more. Although any skin thickness which is effective can be employed, too thick a skin will cause the laminate to remain permanently set when stretched. Generally, where a single skin is less than 30% of the laminate this will not occur. For most heat or time shrink materials, the stretched elastomer must be cooled so that the energy released during stretching does not cause immediate heat activated recovery. Fine tuning of the shrink recovery mechanism can be accomplished by the amount of stretch. This overall control over the shrink recovery mechanism is an extremely important advantage in that it permits adjustment of the recover mechanism of the elastomeric laminate to fit the requirements of a manufacturing process rather than the need to adjust a manufacturing process to fit the shrink recovery mechanism of an elastomer.

One is also able to use skin controlled recovery to control the slow or time shrink recovery mechanism, as with the heat shrink mechanism. This shrink recovery mechanism occurs as an intermediate between instant and heat shrink recovery. Skin layer and stretch ratio control is possible as in the heat shrink mechanism, with the added ability to change the shrink mechanism in either direction, i.e., to a heat or an instant shrink elastomeric laminate.

A time shrink recovery laminate will also exhibit some heat shrink characteristics and vice versa. For example, a time shrink laminate can be prematurely recovered by exposure to heat, e.g., at a time prior to 20 seconds after stretch.

Recovery can also be initiated for most time shrink and some low activation temperature heat shrink recovery laminates by mechanical deformation or activation. In this case the laminate is scored, folded, wrinkled, or the like to cause localized stress fractures that cause localized premature folding of the skin, accelerating formation of the recovered microtextured laminate. Mechanical activation can be performed by any suitable method such as by using a textured roll, a scoring wheel, mechanical deformation or the like.

Figure 10:
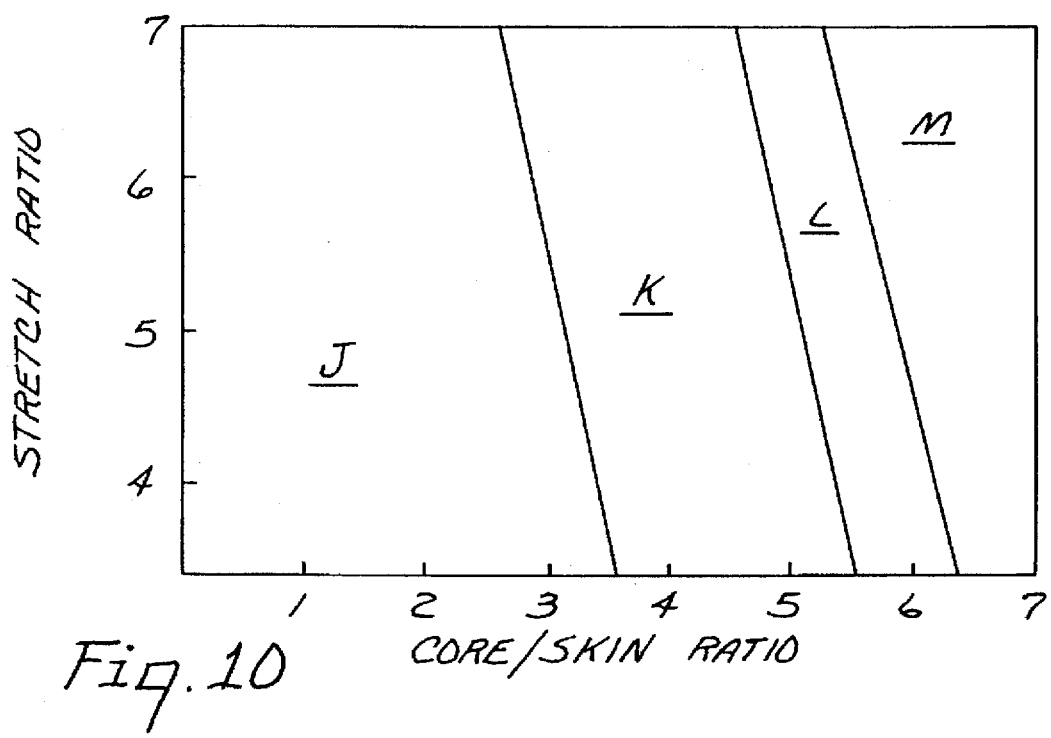
FIG. 10 is a diagram showing the relationship between the shrink mechanism and the core/skin ratio and stretch ratio for an uniaxially stretched film.

FIG. 10, for a polypropylene/styrene-ethylene-butylene-styrene (SEBS)/polypropylene laminate, indicates the possible control of the shrink recovery mechanism for a uniaxially stretched laminate. The numbers on the X-axis are the core thickness to skin thickness ratios, and therefore, the left hand side represents thick skin constructions, and the right hand side represents thin skin constructions. The Y-axis is the stretch ratio employed.

At very thick skins, there is almost no surface microstructure produced at any stretch ratio, even with the application of heat; no shrink region J of FIG. 10. With a core/single skin ratio of about 3 to 5 and 500% stretch, the laminate requires applied heat to recover fully after it has been stretched; heat shrink region K. With a ratio of from about 6 to 7, the structure recovers slowly at ambient conditions, which can also be controlled with heat; time shrink region L. From a ratio of about 6 on up, the laminate will essentially instantly recover; i.e. it snaps back; instant shrink region M. For other elastomeric laminate compositions this relationship will remain valid but the ratios which define the transition from one relaxation zone to another will change.

Diagram 10 also shows the effect of the stretch ratio on the shrink mechanism. Generally, increasing the stretch ratio will modify a laminate shrink mechanism from no shrink to heat shrink to time shrink to instant shrink.

It was also noted that for most elastomeric laminates over a core/skin ratio of about 3 to somewhat above 7, the laminate retained a relatively constant width after it had been restretched. Specifically, if the width of the stretched and recovered material is measured, and if the film is restretched and measured or allowed to recover again and measured, the width remains within at least 20% of its first measured stretch width, preferably within at least 10%. This non-necking characteristic helps prevent the laminate from biting into the skin of a wearer when it is used in a garment. Generally, the skin layer will hinder the elastic force of the core layer with a counteracting resisting force. The skin will not stretch with the elastomer after the laminate has been activated, the skin will simply unfold into a rigid sheet. This reinforces the core, resisting or hindering the contraction of the elastomer core including its necking tendency.

Figure 20:
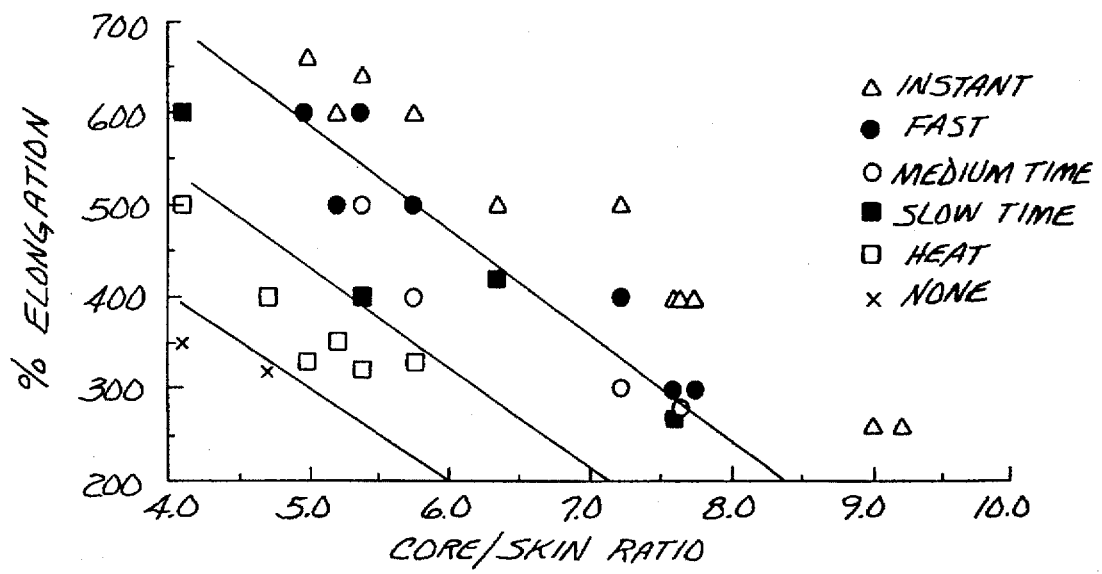
FIG. 20 is a diagram showing the relationship between the shrink mechanism and the core/skin ratio and stretch ratio for a second uniaxially stretched film.

FIG. 20 shows a second shrink mechanism diagram for polypropylene/styrene-isoprene-styrene (SIS)/polypropylene laminates prepared in accordance with those of Example 29. As can be seen, the change in skin layer effects the shrink mechanisms yet the general relationship between the core/skin ratio and the stretch ratio to the shrink mechanism remains the same.

Although the above FIGS. 10 and 20 are illustrative of only particular sets of starting materials and thicknesses they do represent the relationship between the layer ratios and stretch ratio to the shrink mechanism of the laminate. Other variables will affect the above relationship such as overall laminate thickness and the presence of tie layers. However, the general relationship between the core/skin ratio and the stretch ratio to the relaxation method will still be present.

Additives to the core layer discussed above can significantly affect the shrink recovery mechanism. For example, stiffening aids such as polystyrene can shift an otherwise heat shrinkable laminate into a time or instant shrink laminate. However, the addition of polypropylene or linear low density polyethylene (less than 15%) to a styrene/isoprene/styrene block copolymer core resulted in exactly the opposite effect, namely transforming time or instant shrink laminates to heat shrink or no shrink laminates. However, the possibility of polyolefin use in the elastomeric core layer is significant from a processing standpoint in permitting limited recycling of off batches and it can lower extruder torque.

A further unique feature of the present invention lies in the ability to significantly reduce the coefficient of friction (C.O.F.) of the elastomeric laminate. The microtexturing is the major factor contributing to this C.O.F. reduction which, as discussed above, is controllable not only by the manner in which the laminate is stretched but also by the degree of stretch, the overall laminate thickness, the laminate layer composition and the core to skin ratio. The dependence of C.O.F. on core/skin ratio is shown in Table II. As the ratio increases the C.O.F. decreases. Thus, fine texture yields lower C.O.F. values. Preferably, the C.O.F. of the laminate to itself will be reduced by a factor of 0.5 and most preferably by at least a factor of 0.1 of the microtextured laminate to itself in the direction of stretch, when a microstructured surface is formed in accordance with the invention, as compared to the as cast laminate. This ability to reduce C.O.F. is extremely advantageous as it contributes to a softer texture and feel for the laminate, which is desirable for use in the medical and apparel fields.

Figure 8:
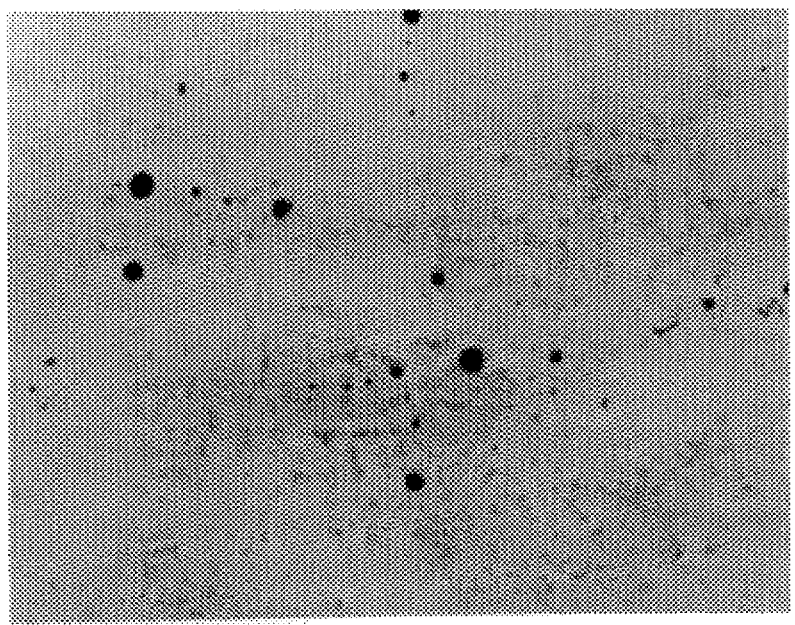
FIG. 8 is a photograph of a unstretched laminate of the invention that has been marked with ink.
Figure 9:
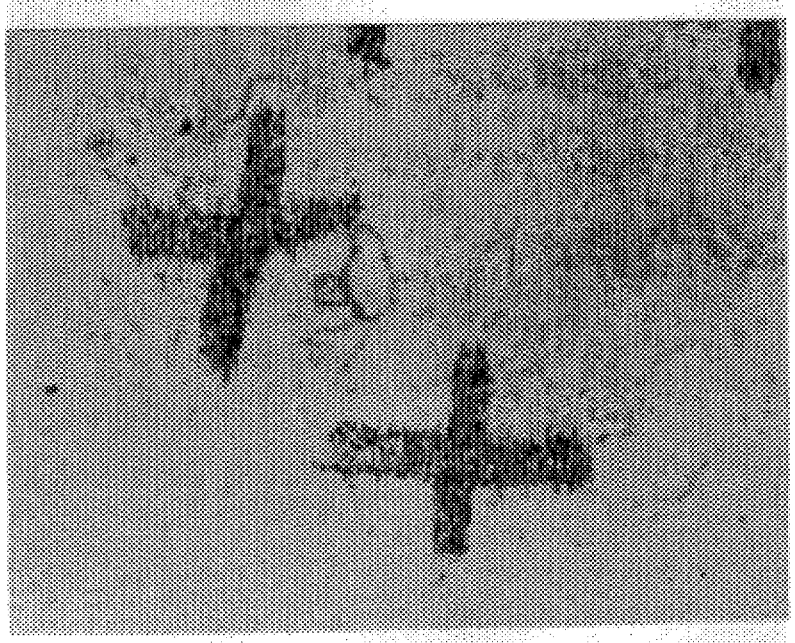
FIG. 9 is a photograph of the stretched laminate of FIG. 8 marked with the same ink.

Writability of the film is also increased by the microstructured surface that results when the stretched film recovers. Either organic solvent or water-based inks will tend to flow into the microstructured surface channels and dry there. FIG. 8 shows the surface of an unstretched, untextured laminate where the ink clearly beads up. FIG. 9 demonstrates the improvement in writability for the laminate of FIG. 8 after stretching and recovery to create a microtextured surface (see example 26). The more viscous the ink the less it will tend to wick in the microchannels of the surface and hence bleed. Similarly, the more the surface attraction between the skin layer and the ink, the better will be the writing characteristics of the microstructured surface. The writing surface characteristics of the film can also be altered with conventional additive or surface treatment techniques to the extent that they do not interfere with microtexturing.

The laminates of the present invention may be formed by any convenient layer forming process such as pressing layers together, coextruding the layers or stepwise extrusion of layers, but coextrusion is the presently preferred process. Coextrusion per se is known and is described, for example, in U.S. Pat. No. 3,557,265 to Chisholm et al and U.S. Pat. No. 3,479,425 to Leferre et al. Tubular coextrusion or double bubble extrusion is also possible. The layers are typically coextruded through a specialized die and/or feedblock that will bring the diverse materials into contact while forming the laminate.

FIG. 1 shows a three-layer laminate construction in cross section, where the 3 is the elastomeric layer and 2 and 4 are the skin layers, which may be the same polymer or different polymers. This layer arrangement is preferably formed by a coextrusion process.

Figure 4:
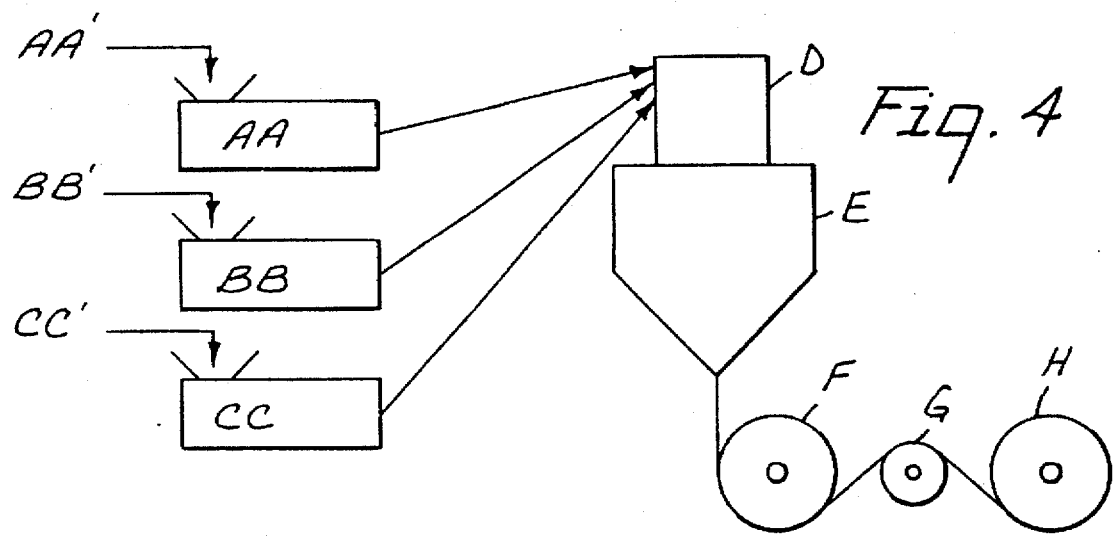
FIG. 4 is a schematic representation of a process and apparatus used to coextrude the laminates of the invention.

One particularly advantageous coextrusion process is possible with special multilayer, e.g. a three-layer, combining adapters made by Cloeren Co., Orange, Tex. These adapters are described in U.S. Pat. No. 4,152,387 to Cloeren, which is incorporated herein by reference. Streams of thermoplastic materials flowing out of extruders at different viscosities are separately introduced into the adapter, containing back pressure cavities and flow restriction channels, and the several layers exiting the flow restriction channels converge into a melt laminate. The combining adapter is used in conjunction with extruders supplying the thermoplastic materials to be laminated. Such a scheme for producing the present invention is shown schematically in FIG. 4, for a three layer adapter. AA, BB, and CC are extruders. AA', BB' and CC' are streams of thermoplastic materials flowing into the feedblock or manifold die. D is the 3 or more (e.g., 5-layer) layer feedblock. E is the die, F is a heated casting roll, and G and H are rolls to facilitate take-off and roll-up of the laminate.

The die and feedblock used are typically heated to facilitate polymer flow and layer adhesion. The temperature of the die depends upon the polymers employed and the subsequent treatment steps, if any. Generally the temperature of the die is not critical but temperatures are generally in the range of 350° to 550° F. (176.7° to 287.8° C.) with the polymers exemplified.

Whether the laminate is prepared by coating, lamination, sequential extrusion, coextruston or a combination thereof, the laminate formed and its layers will preferably have substantially uniform thicknesses across the laminate. Preferably the layers are coextensive across the width and length of the laminate. With such a construction the microtexturing is substantially uniform over the elastomeric laminate surface. Laminates prepared in this manner have generally uniform elastomeric properties with a minimum of edge effects such as curl, modulus change, fraying and the like.

The laminate of the invention has an unlimited range of potential widths, the width limited solely by the fabricating machinery width limitations. This allows fabrication of microtextured elastomers for a wide variety of potential uses.

After forming the laminate it is stretched past the elastic limit of the skin, which deforms. The laminate then is recovered instantaneously, with time or by the application of heat, as discussed above. For heat recovery the temperature of activation is determined by the materials used to form the laminate in the first instance. For any particular laminate the activation temperature, either $T_{a-50}$ or $T_{a-90}$, can be adjusted by varying the skin/core ratio of the laminate, adjusting the percent stretch or the overall laminate thickness. The activation temperature used for a heat shrink laminate is generally at least 80° F. (26.7° C.), preferably at least 90° F. (32.2° C.) and most preferably over 100° F. (37.8° C.). When heat activated the stretched laminates are quenched on a cooling roller, which prevents the heat generated from the elongation from activating laminate recovery. The chill roll is below the activation temperature.

Figure 2:
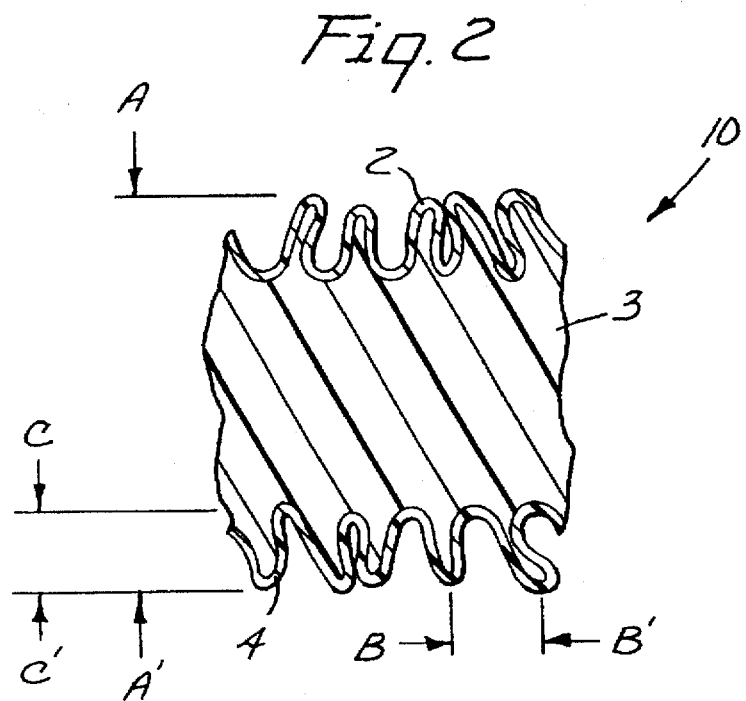
FIG. 2 is the cross-sectional segment of FIG. 1 of the laminate with microstructuring caused by uniaxially stretching a film of the invention.

FIG. 2 is a schematic diagram of the common dimensions which are variable for uniaxially stretched and recovered laminates. The general texture is a series of regular repeating folds. These variables are the total height A–A', the peak-to-peak distance B–B' and the peak-to-valley distance C–C'. These variables were measured for a series of polyolefin/ styrene-isoprene-styrene/polyolefin laminates. General ranges for A-A', B-B' and C-C' were noted. For total height (A-A'), the range measured was from 0.79 to 32 mils (0.02 to 0.81 mm). For peak-to-peak distance (B-B'), or the fold period, the measured range was from 0.79 to 11.8 mils (0.02 to 0.30 mm). For peak-to-valley distance (C-C'), the measured range was from 0.04 to 19.7 mils (0.001 to 0.5 mm). These ranges are only exemplary of the surface characteristics obtainable by the practice of the present invention. Laminates of other compositions will demonstrate different microstructures and microstructure dimensions. It is also possible to obtain dimensions outside the above ranges by suitable selection of core/skin ratios, thicknesses, stretch ratios and layer compositions.

A further unique feature of the invention laminate is depicted in FIG. 2. That is when the material is stretched and recovered uniaxially, regular, periodic folds are generally formed. That is for any given transverse section the distance between adjacent peaks or adjacent valleys is relatively constant.

Figure 3:
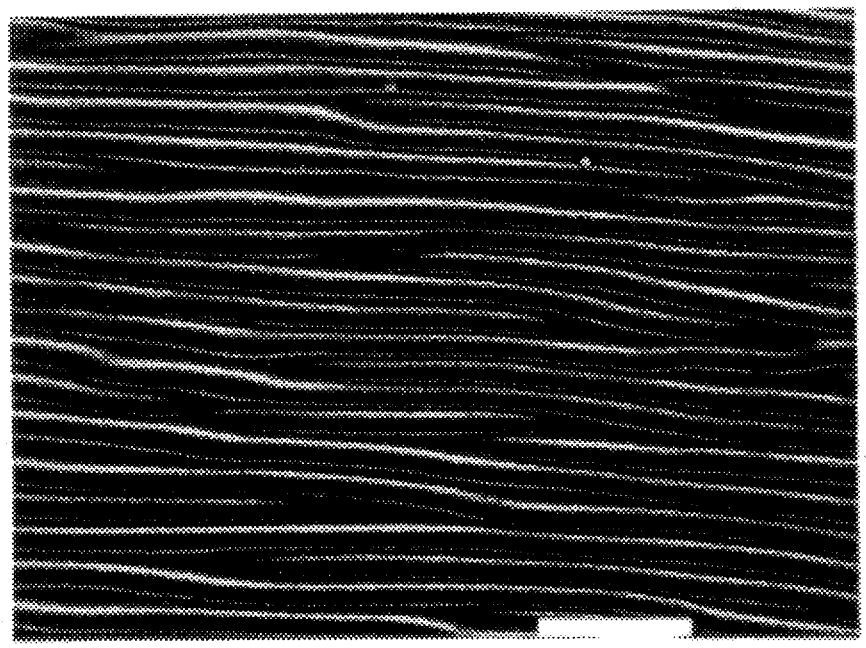
FIG. 3 is a scanning electron micrograph (200×) of a microstructured laminate of the invention that has been uniaxially stretched.

FIG. 3 shows a scanning electron micrograph of the surface of a polybutylene/styrene-isoprene-styrene (SIS)/polybutylene laminate of Example 6 which has been stretched past the elastic limit of the outer skin layers in the longitudinal direction and allowed to recover to form a microstructured surface. The microstructured surface corresponds to that shown schematically in FIG. 2.

The microstructured surface consists of relatively systematic irregularities whether stretched uniaxially, as was the FIG. 3 laminate, or biaxially. These irregularities increase the opacity and decrease the gloss of the surface layers of the laminate, but generally do not result in cracks or openings in the surface layer when the layer is examined under a scanning electron microscope.

Microtexturing also affects the properties of the formed film. Uniaxial stretching will activate the film to be elastic in the direction of stretch. Biaxial stretching will create unique surfaces while creating a laminate which will stretch in a multitude of directions and retain its soft feel, making the so stretched laminate particularly well suited for garment use.

It has also been found that the fold period of the microstructured surface is dependent on the core/skin ratio, as shown in Example 3. The periodicity is also indicative of the texture of the surface as per Table II and FIGS. 12-14, which figures show fine, medium and coarse textures, respectively. This is again another indication of the control possible by careful choice of the parameters of the present invention.

It has also been found that the manner in which the film is stretched effects a marked difference in the texture of the microstructured surface. For example, the extruded multilayer film can be stretched uniaxially, sequentially biaxially, or simultaneously biaxially, with each method giving a unique surface texture and distinct elastomeric properties. When the film is stretched uniaxially, the folds are microscopically fine ridges, as per FIG. 3, with the ridges oriented transversely to the stretch direction.

Figure 6:
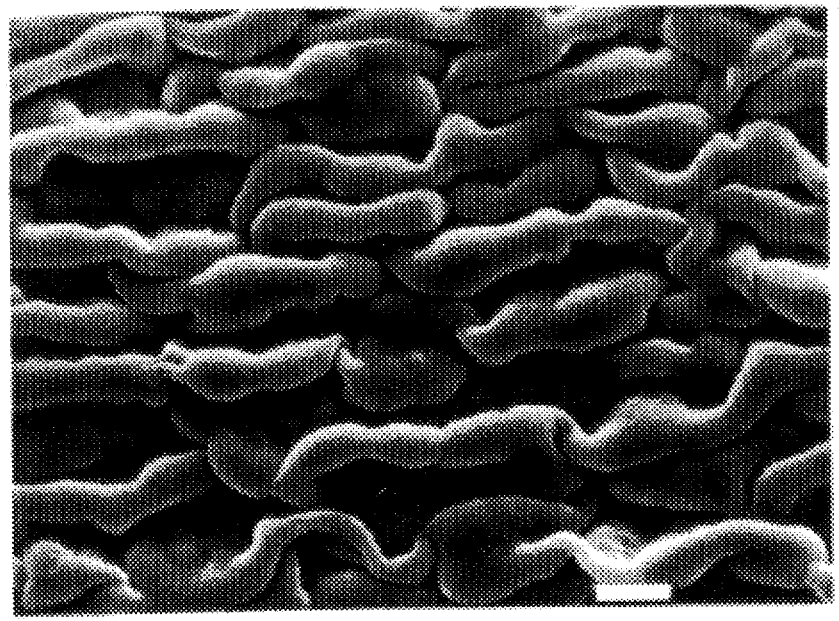
FIG. 6 shows an electron micrograph (1000×) of a sample of the present invention which was sequentially biaxially stretched.
Figure 7:
FIG. 7 shows an electron micrograph (1000×) of a sample of the present invention with a polyethylene skin which was simultaneously biaxially stretched.
Figure 15:
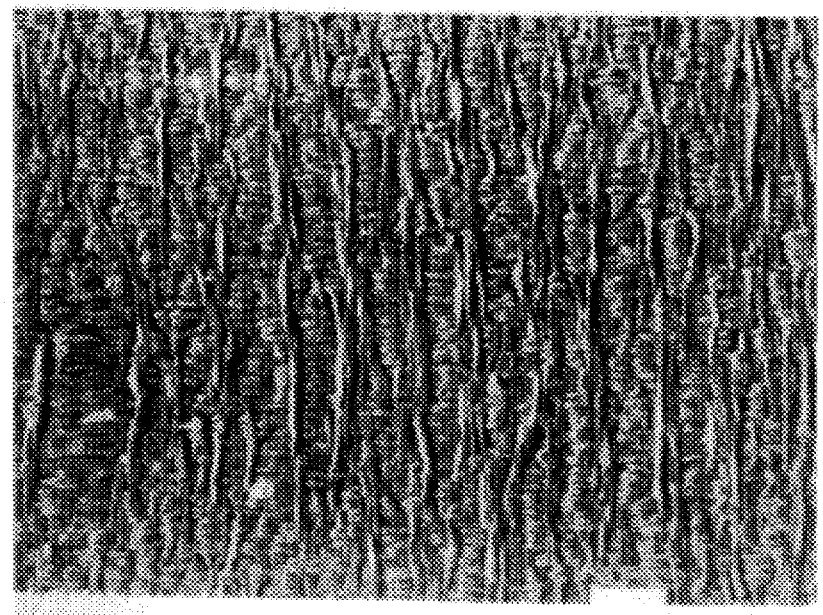
FIGS. 15 and 16 are scanning electron micrographs (100×) of the surface of laminates which have been sequentially biaxially stretched.
Figure 16:
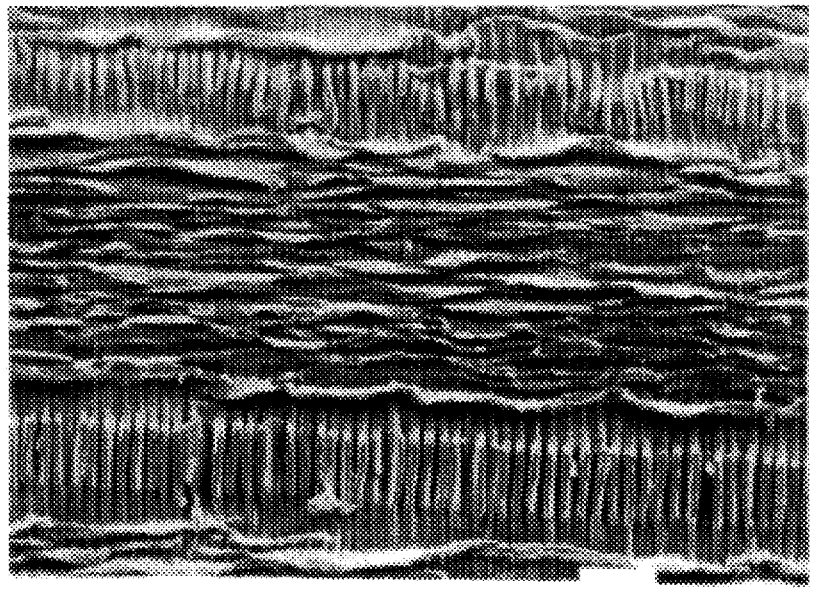
Figure 18:
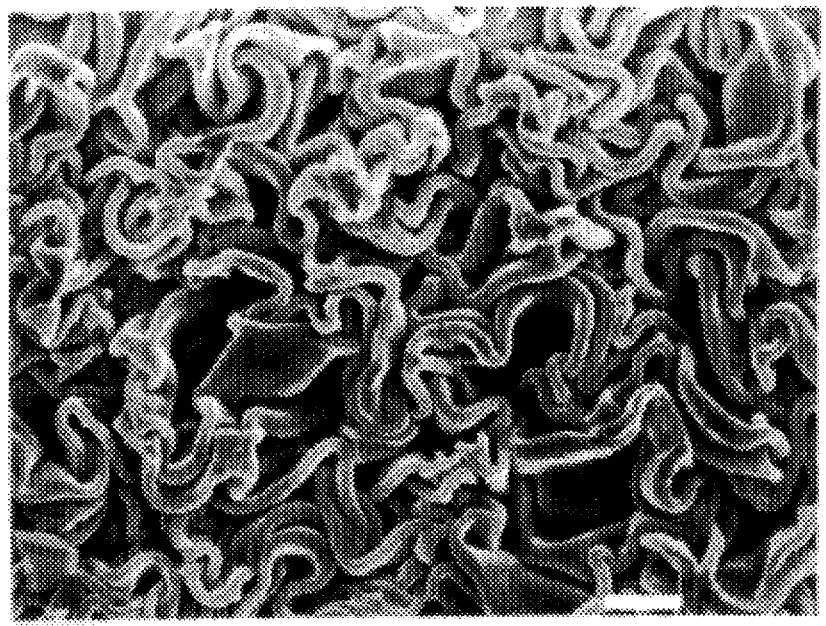
FIG. 18 is a scanning electron micrograph (100×) of a simultaneously biaxially stretched invention laminate which has a polypropylene skin.

When the laminate is stretched first in one direction and then in a cross direction, the folds formed on the first stretch become buckled folds and can appear worm-like in character, as shown in FIG. 6, with interspersed cross folds as in FIGS. 15 or 16. FIG. 6 is the laminate of Example 6, FIG. 15 is a laminate of LLDPE/SIS/LLDPE (linear low density polyethylene) with a core/skin ratio of 15.3 and FIG. 16 is a laminate of PP/SIS/PP with a core/skin ratio of 18 (Example 24). Other textures are also possible to provide various folded or wrinkled variations of the basic regular fold. When the film is stretched in both directions at the same time the texture appears as folds with length directions that are random, as shown in FIG. 7 (a laminate prepared as per Example 19A with skin/core/skin thicknesses of 5/115/5 microns respectively) or FIG. 18 (Example 24). Using any of the above methods of stretching, the surface structure is also dependent, as stated before, upon the materials used, the thickness of the layers, the ratio of the layer thicknesses and the stretch ratio.

The unique continuous microstructured surfaces of the invention can be altered and controlled by the proper choice of materials and processing parameters. Differences in the material properties of the layers can change the resulting microtextured skin, but it has been found that by the careful choice of the layer ratios, total laminate film thickness, the number of layers, stretch degree, and stretch direction(s) it is possible to exercise significant control over the microstructure of the laminate surface.

The degree of microtexturing of elastomeric laminates prepared in accordance with the invention can also be described in terms of increase in skin surface area. Where the laminate shows heavy textures the surface area will increase significantly. This is demonstrated for linear low density polyethylene (LLDPE)/SIS/LLDPE laminates in Table VIII, Example 16. In this example, as the stretch ratio increases so does the percent increase in surface area, from the unstretched to the stretched and recovered laminate; from 280 at a stretch ratio of 5, to 530 at a stretch ratio of 12. Generally, the microtexturing will increase the surface area by at least 50%, preferably by at least 100% and most preferably by at least 250%. The increase in surface area directly contributes to the overall texture and feel of the laminate surface.

Increased opacity of the skin and hence the laminate also results from the microtexturing. Generally, the microtexturing will increase the opacity value of a clear film to at least 20%, preferably to at least 30%. This increase in opacity is dependent on the texturing of the laminate with coarse textures increasing the opacity less than fine textures. The opacity increase is also reversible to the extent that when restretched, the film will clear again.

Figure 17:
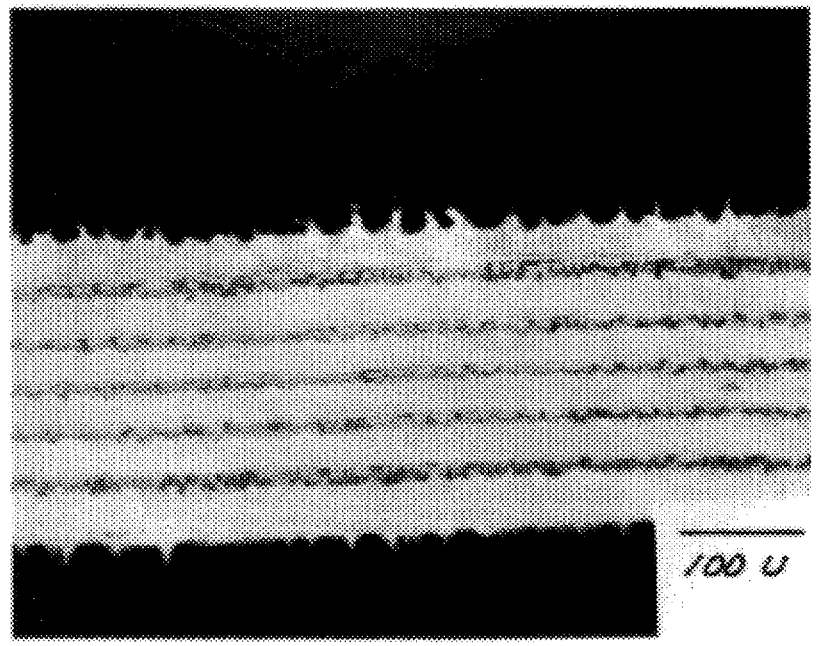
FIG. 17 is a scanning electron micrograph (100×) of a 13 layer laminate of the invention.

It is also possible to have more than one elastomeric core member with suitable skins and/or tie layer(s) in between. Such multilayer embodiments can be used to alter the elastomeric and surface characteristics of the laminate. An example of such a laminate is shown in FIG. 17 which is formed from 6 three-layer laminates.

With certain constructions the microtextured skin layers may tend to delaminate and/or the underlying elastomer may tend to degrade over time. This tendency may particularly occur with ABA block copolymers. Residual stress created during the stretching and recovery steps of activating the material to its elastomeric form can accelerate this process significantly. For those constructions prone to such degradation or delamination, a brief relaxing or annealing following activation may be desirable. The annealing would generally be above the glass transition point temperature ($T_g$) of the elastomer, above the B block $T_g$ for ABA block copolymers, but below the skin polymer melting point. A lower annealing temperature is generally sufficient. The annealing will generally be for longer than 0.1 seconds, depending on the annealing temperature. With commercial ABA block copolymers (e.g., Kraton™ 1107) an annealing or relaxing temperature of about 75° C. is found to be sufficient.

The skin layer-to-core layer contact in the stretched and activated film has been observed to vary depending on the skin and core compositions. With certain preferred constructions, the core and skin remain in full contact with the core material, filling the folds formed in the skin layers as shown in FIG. 2. This construction is extremely durable and not as subject to delamination, particularly when annealed following activation. A variation of this continuous contact construction is also possible where the elastomer fills the skin folds but is observed to cohesively fail under the folds. It is believed this occurs with thicker and/or more rigid skins that expose the underlying elastic to more concentrated stresses during relaxation. An entirely different skin/core adhesion mode is also possible. Namely, the core in some cases can completely retract from the skin under the folds, but remain sufficiently attached such that the skin does not delaminate (see Example 32, adhesive failure). This construction is not as desirable generally as during use it is more easily subject to delamination as well as exposing the core to air which may accelerate degradation of the elastomer.

The laminate formed in accordance with the above description of the invention will find numerous uses due to the highly desirable properties obtainable. For example, the microtexture gives the elastomeric laminate a soft and silky feel. The laminate can further be non-necking. This renders the elastomeric laminate particularly well suited for a variety of commercially important uses particularly in the garment area, where elastic webs are used in areas to engage or encircle a body portion alone or as part of a garment. Examples of such garments include disposable diapers, adult incontinence garments, shower caps, surgical gowns, hats and booties, disposable pajamas, athletic wraps, clean room garments, head bands for caps or visors or the like, ankle bands (e.g., pant cuff protectors), wrist bands, rubber pants, wet suits and the like.

When used as rubber pants or possibly as surgical gowns, the laminate could comprise substantially the entire garment in which case the garment itself as a whole would engage the body.

The laminate can be extensively used in disposable diapers, for example as a waistband, located in either the front or side portions of the diaper at waist level, as leg elastic, as a soft outer cover sheet or in adjustable slip-on diapers, where the elastomeric laminate could be used as, or in, side panels around the hip that create a tight fitting garment. The laminates can be applied as continuous or intermittent lengths by conventional methods. When, applied, a particular advantage of the laminate is the ability to use thin elastomers with high stretch ratios. This creates a great deal of gathering or shirr when applied to the garment when stretched, which gives the shirred portion a cushion-like feel, despite the thinness of the elastomer.

Garments often are shirred to give a snug fit. This shirring can be easily obtained by applying the laminate while in an unstable stretched condition and then affecting the shirr by application of heat. The elastomeric laminate can be adhered to the garment by ultrasonic welding, heat sealing and adhesives by conventional methods.

The controlled relaxation obtainable by adjusting the layer ratios, stretch ratio and direction, and layer composition makes the elastomeric laminate of the invention well suited to high speed production processes where heat activated recovery can be controlled easily by hot fluids such as hot air, microwaves, UV radiation, gamma rays, friction generated heat and infrared radiation. With microwaves, additives, such as iron whiskers, nickle powder and aluminum flakes, may be needed to ensure softening of the skin to effect skin controlled recovery.

Figure 5:
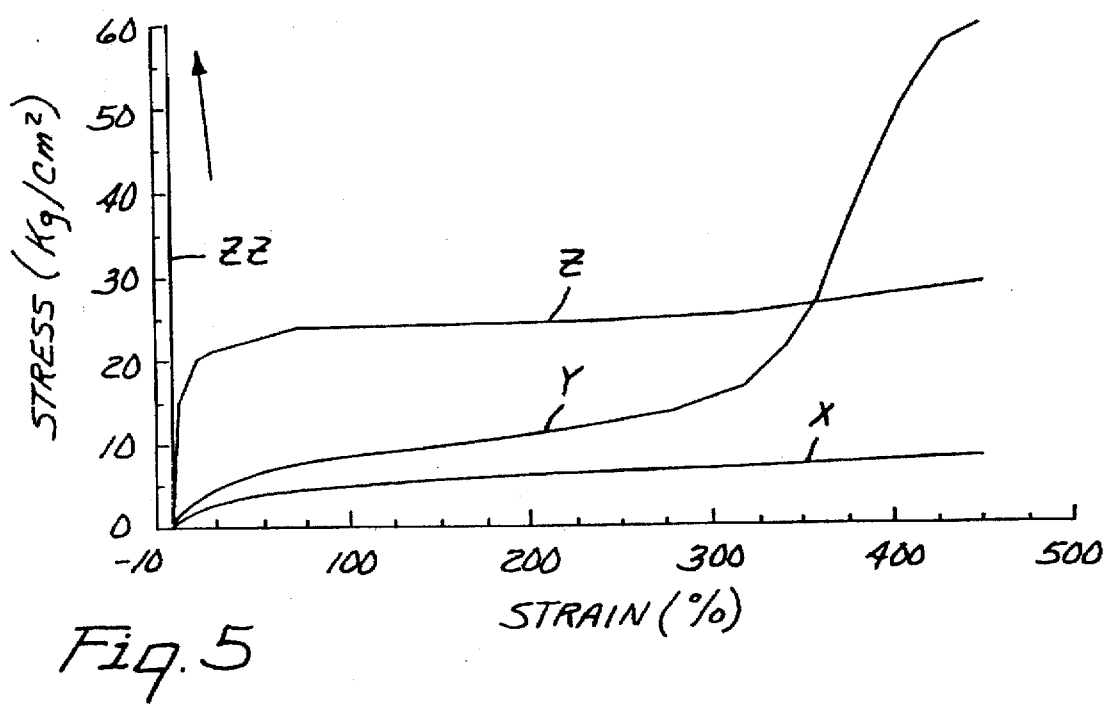
FIG. 5 is a diagram showing the stress-strain characteristics of a laminate and its component layers.

The counter balancing of the elastic modulus of the elastomeric layer and the deformation resistance of the skin layer also modifies the stress-strain characteristics of the laminate. The modulus therefore can be modified to provide greater wearer comfort when the laminate is used in a garment. For example, a relatively constant stress-strain curve can be achieved. This relatively constant stress-strain curve can also be designed to exhibit a sharp increase in modulus at a predetermined stretch percent, i.e., the point at which the skin was permanently deformed when activated as shown in FIG. 5, line Y. Prior to activation, the laminate is relatively rigid, line Z of FIG. 5, i.e., having a high modulus imparted due to the, skin layer. The non-activated or non-stretched laminate is easier to handle and much better suited to high speed production processes than would be a conventional elastic. To achieve these benefits, the skin can be either an inner layer, an outer layer or both. In FIG. 5 line ZZ is the skin alone and line X is the elastomeric layer alone.

The microtexturing, with the resulting ability to form enclosed or partially enclosed spaces on the skin and the ability to form sheets of widely varying lengths and widths, makes the microtextured laminate also useful in its sheet form as a wipe. Further, the polymeric laminate will easily electrostatically charge when rubbed. This ability coupled with the enclosed spaces makes sheet laminates useful as dust wipes, or as dust mats (e.g., in a clean room). Further, the polymer skin will often attract and store oils.

Another significant advantage with the microtextured laminate is the ability to form laminate films or ribbons with significant aesthetic appeal. It is highly desirable to provide ribbons or films with muted or opaque colors. It has been found that by coloring the inner core layer the stretched and recovered ribbon or film has novel visual appeal. The microtextured skin creates an opaquely colored film that appears velvet-like. The opacity is believed to be due primarily to light scattering in the microtextured skin layer. Velvet-like means that there are color variations depending on the angle one views the laminate with an overall soft look from the microtexturing. It is believed that this visual effect will still remain with slight coloring of the skin layers, with the possibility of added color dimensions, The following Examples are provided to illustrate presently contemplated preferred embodiments and the best mode for practicing the invention, but are not intended to be limiting thereof.

EXAMPLE 1

A five-layer laminate was prepared from two outer layers of 5.08 cm by 5.08 cm, 2000 molecular weight polystyrene and two layers of 5.08 cm by 5.08 cm of 2 mil (0.0508 mm) thick linear low density polyethylene (LLDPE) film (Dow™ 61800, Dow Chemical Corp., Midland, Mich.) and a core layer of 5.08 cm by 5.08 cm of 125 mil (3.175 mm) thick styrene-isoprene-styrene (SIS) film (Kraton™ 1107, available from Shell Chemical Company, Beaupre, Ohio) by heating at 160° C. under 2000 pounds per square inch (140 kilograms per square cm) of a flat press. The resulting film laminate was about 5 mil (0.127 mm) thick. The polystyrene layers were a processing aid to help form a uniform layered film. The thin brittle polystyrene layers of the laminate were peeled away, and a clear film remained. After stretching the clear film by hand to 500%, and allowing it to recover, a smooth and pleasing surface was observed with the naked eye, and surprisingly, examination under a microscope disclosed a continuous, deeply textured, microstructured surface. Since this sample was uniaxially stretched, fine ridges were observed, oriented transversely to the stretch direction, said ridges having a height to width ratio of about 2 to 1.

EXAMPLE 2

A continuous coextrusion was carried out to prepare a three-layer laminate with two outer skin layers of LLDPE and a core layer of SIS using polymers as described in Example 1. Three laminates of 8.5, 4.7, and 3 mil (215, 120 and 78 microns) thickness were prepared using a Rheotec (Rheotec Extruder Co., Verona, N.J.) extruder to feed the SIS layer from a tee union into the center of a cross union and a Berlyn™ (Berlyn Corp., Worchester, Mass.) extruder was used to feed the two LLDPE layers into the two opposite sides of the cross union and then the three laminated layers of film were drawn from the 425° F. (218° C.) die in widths of 18 inches (45.7 cm). The laminates had skin/core, skin thicknesses in microns of 20/175/20, 16/90/14 and 10/60/8, respectively, determined under a light microscope. After the film was stretched past the elastic limit of the outer skin layers, it deformed and demonstrated a microstructured surface upon recovery. When initially uniaxially stretched about 500%, these laminates necked down, width wise, to about 40% of their unstretched width. Upon subsequent restretching to about 500% the films surprisingly necked down very little as shown in Table I.

TABLE I

| Sample | % Reduction in Width Thickness upon Restretching |
|---|---|
| 78 microns | 5.2 |
| 120 microns | 3.2 |
| 215 microns | 2.8 |

The films thus essentially remained constant in width after initial stretching. Not all stretched films will show this non-necking property. The non-necking is a property of the unique unfolding of the stretched surface layers of the present invention, and is a function of the skin thickness and modulus, i.e., strength. This strength must be high enough to prevent width contraction of the core layer upon re-stretching. That is, it is a balance of skin and core forces. Very soft or very thin skinned materials, therefore, need to be thicker for the laminate to possess this property.

EXAMPLE 3

A continuous coextrusion was carried out to prepare three-layer laminates with two outer layers of polypropylene and a core elastomeric layer of a styrene-isoprene-styrene block copolymer. A 2 in (5.1 cm) screw diameter Berlyn™ extruder was used to feed the elastomer layer (Kraton™ 1107, Shell Chemical Company, Beaupre, Ohio) and a Brabender™ 1.25 inch (3.18 cm) screw diameter extruder (available from C. W. Brabender Instruments, Inc., N.J.) was used to feed the two polypropylene (Escorene™ 3085, available from Exxon Corporation, Houston, Tex.) layers into the Cloeren™ feedblock, and were extruded through a single manifold 18 inch (46 cm) wide film die. The film was cast onto a 60° F. (16° C.) cast roll at 14.7 ft/min (509 cm/min) at varying total caliper as described in Table II. Films of varying outer layer thickness were prepared.

The films were tested for relaxation by initially uniaxially stretching, each sample by hand to just short of its breaking point, which was generally about 650%, releasing the sample, and observing any recovery. Recovery after initial draw was then categorized as instantaneous recovery (I), slow recovery with time (T), heat required for recovery (H) and permanent deformation (P), i.e. no significant recovery. Results are shown in the following table.

TABLE II

| SAMPLE NO. | TOTAL SKIN THICKNESS (microns) | CORE THICKNESS (microns) | CORE THICKNESS SKIN THICKNESS | RECOVERY | TEXTURE OF LAMINATE | % Change in Width upon Restretching sample | C.O.F. | Periodicity |
|---|---|---|---|---|---|---|---|---|
| A | 5 | 90 | 18 | I | F | 1.4 | | — |
| B | 8 | 145 | 18 | I | F | 2.8 | 0.59 | 10μ |
| C | 12 | 175 | 14.6 | I | M | 2.0 | 0.67 | 45μ |
| D | 7 | 54 | 7.7 | I | F | 2.0 | | |
| E | 14 | 100 | 7.1 | T | C | 0 | 0.75 | 90μ |
| F | 8 | 48 | 6 | T–H | F | 0 | | |
| G | 20 | 45 | 2.25 | P | Smooth | Did not recover | | |

Figure 12:
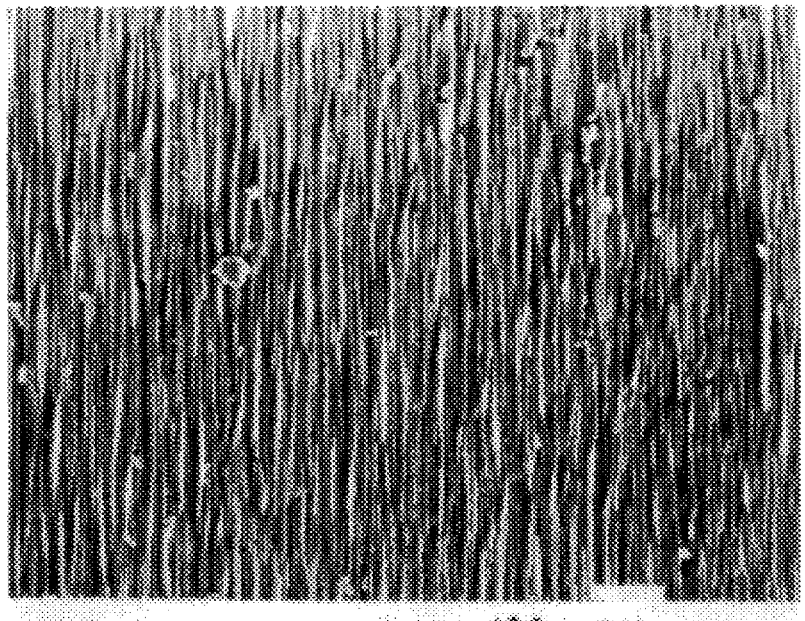
FIGS. 12, 13 and 14 show scanning electron micrographs (100×) of fine, medium and coarse textures, respectively, for a series of invention laminates with the same core and skin compositions.
Figure 13:
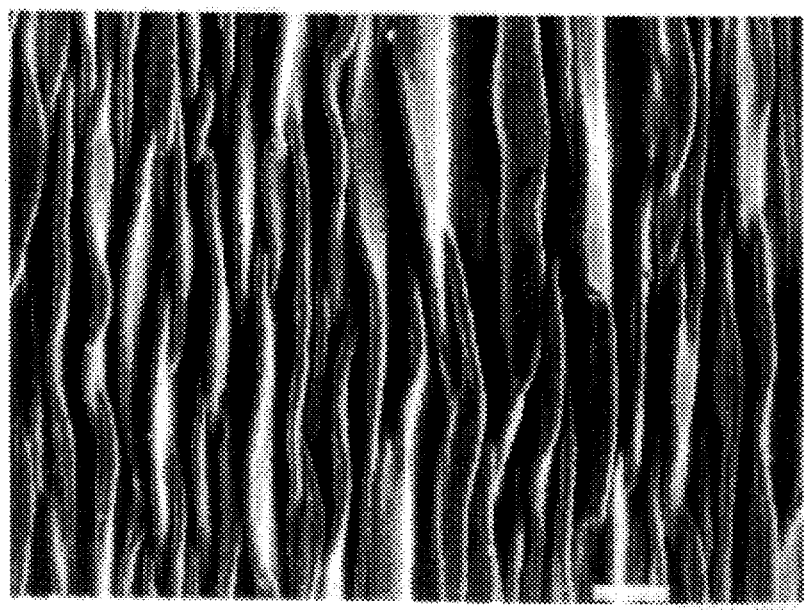
Figure 14:
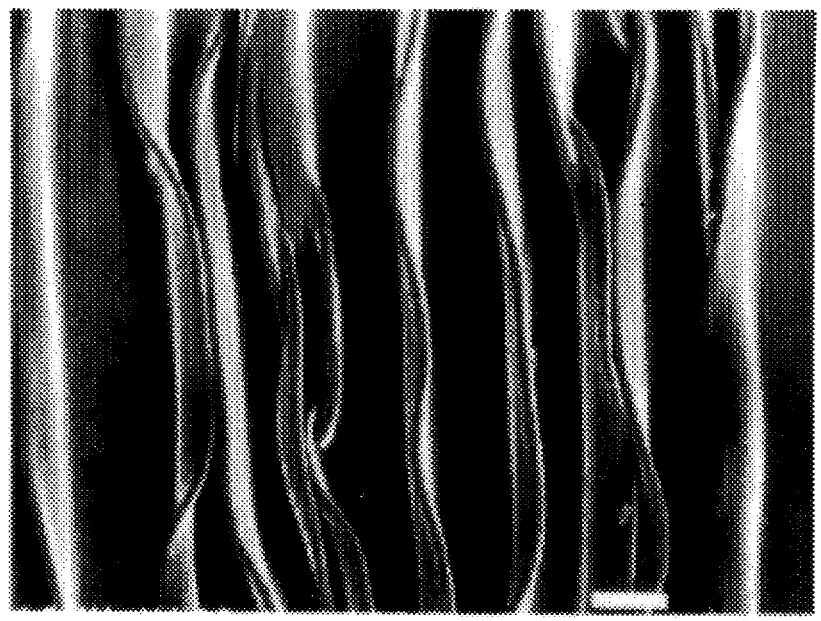

The texture of the laminate is evaluated both visually and by touch after recovery and classified as fine (F), medium (M), coarse (C) or smooth (no texture discerned). The texture was also measured objectively in samples B, C and E by the periodicity (distance between folds) of the samples. FIGS. 12, 13 and 14 show scanning electron micrographs (100×) of samples B, C and E, respectively. It is noted that as the regular folds get coatset they also appear larger and more widely spaced. Although the large folds are more subject to having more random peak to peak distances they are still quite regularly spaced.

The samples were also tested for necking characteristics expressed as % change in width upon restretching of the sample. Although necking was not significant for any of these samples, generally, as skin thickness fell and the core-to-skin thickness ratio rose, necking increased.

Periodicity and C.O.F. are also shown for samples B, C and D which are both inversely related to the core/skin thickness ratio. The original C.O.F. for the samples was over 3.8, thus the microtexturing produced a significant overall reduction of C.O.F.

EXAMPLE 4

A multilayer laminate was prepared by laminating cast laminates of polypropylene/Kraton™ 1107/polypropylene prepared as in the previous example. The total thickness of each cast laminate was 2.8 mil (0.062 mm). The core/skin ratio was 12:1. The laminated laminate was formed of 6 cast laminates in a hot press at 200° C. at 140 kilograms per square centimeter pressure for five minutes. The formed film was then cooled in a 21° C. water bath. The resulting laminate was 6 mil (0.15 mm) thick and appeared like the cast film but thicker. After stretching approximately 300% and instantaneous recovery, the film displayed a coarse microtextured skin and microtextured inner skin layers as shown in FIG. 17.

EXAMPLE 5

A continuous coextrusion was carried out to prepare three-layer laminates with two outer layers of a 70/30 by weight blend of poly(vinylidene fluoride) (Solef™ 1012, Solvay Co., France) and poly(methyl methacrylate) (VO44, Rohm and Haas Corp., Bristol, Pa.) and a core layer of Kraton™ 1107. A two inch (5.1 cm) diameter Berlyn™ screw extruder at 10 RPM screw speed, was used to feed the core layer polymer and a 2 inch (5.1 cm) diameter screw Rheotec™ extruder, at 25 RPM, was used to feed the skin layer polymer blends into a Cloeren™ feedblock and the melt laminate was extruded through a single manifold die, 18 inches (46 cm) wide (Extrusion Dies, Inc., Chippawa Falls, Wis.), at 420° to 450° F. (215° to 232° C.) onto a 78° F. (26° C.) cast roll at 17.0 or 15.3 revolutions per minute (RPM), respectively. The film laminate thicknesses obtained were 5.5 and 6.0 mil (0.14 and 0.15 mm) with core/skin ratios of 6:1 and 7.5:1, respectively.

Both laminates were stretched 400% and allowed to immediately recover. In each case, a laminate with a fine glossy microtextured surface was obtained.

EXAMPLE 6

A continuous coextrusion was carried out to prepare two distinct three-layer laminates with two outer layers of a 50/50 blend of two polybutylenes resins, Snell™ 0200 and Shell™ 0400, and a core elastomeric layer of Kraton™ 1107. A two inch (95.2 cm) diameter screw Berlyn™ extruder was used to feed the Kraton™ 1107 at a screw speed of 10 RPM. A 1.25 inch (3.18 cm) diameter Brabender™ screw extruder was used to feed the two polybutylene blend layers at screw speeds of 10 and 12 RPM into a Cloeren™ feed block. The laminates were extruded through a single manifold 18 inch (46 cm) wide film die at 430° F. (221° C.) onto a 60° F. (16° C.) cast roll at either 8.8 or 7.6 ft/min (2.7 or 2.3 m/min), maintaining a total caliper of 0.003 inches (0.076 mm) for both samples. This produced two films of varying outer skin thicknesses with the same total laminate thickness. The core/skin ratios were 13:1 and 5:1, respectively.

Also, the same equipment was run at a Brabender™ extruder speed of 35 RPM and a cast roll speed of 8.6 ft/min (2.6 m/min), all other conditions the same as above, to give a 0.005 inch (0.127 mm) thick laminate (comparative) with thick overall skin layers, and a core/skin ratio of 2.6:1.

The texture for each sample was noted after each laminate was stretched by hand just short of its breaking point, about 4:1, and allowed to recover, the first two runs instantly and the third (.comparative) with heat. The textures were classified as very fine, fine and none. This data is shown in Table III below.

TABLE III

| Brabender™ Speed (RPM) | Cast Roll Speed (cm/min.) | Total Film Thickness (cm) | Texture |
| --- | --- | --- | --- |
| 10 | 268 | 0.0081 | very fine |
| 12 | 232 | 0.0081 | fine |
| 35 | 262 | 0.013 | none |

EXAMPLE 7

A continuous coextrusion was carried out to prepare five layer laminates with two outer layers of linear low density polyethylene, tie layers of Elvax™ 260 (EVA-ethylene vinyl acetate) (available from Dupont Corporation, Wilmington, Del.) and a core elastomer layer of styrene-isoprene-styrene block copolymer. A two inch (5.1 cm) screw diameter, 4D ratio Berlyn™ extruder was used to feed the elastomer layer (Kraton™ 1107). A Rheotec™ two inch (3.18 cm) screw diameter extruder was used to feed the two polyethylene layers, and a one inch (2.54 cm) screw diameter 3M-made extruder was used to feed the two Elvax™ layers into a Cloeren™ feedblock.

The laminates were extruded through a single manifold 18 inch (46 cm) wide film die at 375° F. (190° C.) onto a 60° F. (16° C.) cast roll at varying total caliper or thickness as described in Table IV. Films of varying layer thickness were thus prepared. This example also demonstrates how casting roll speed affects film thickness.

The EVA tie layers add bonding strength between the LLDPE outer layers and the SIS core layer, resulting in a more durable laminate than such a film without the EVA, yet does not interfere with the way the laminate behaves with respect to surface texture. This tie layer is, of course, very thin compared to the other layers.

TABLE IV

| | PROCESSING CONDITIONS FOR SAMPLES | | | | | | |
| --- | --- | --- | --- | --- | --- | --- | --- |
| NO. | BERLYN+ RPM | RHEOTEC++ RPM | CASTING ROLL SPEED (RPM) | NIPP ROLL SPEED (RPM) | FILM THICKNESS (microns) | SURFACE* TEXTURE | 1" EXT.' RPM |
| 7A | 30 | 8 | 15 | 15 | 132.0 | F | 24 |
| 7B | 30 | 8 | 15 | 15 | 132.0 | F | 24 |
| 7C | 30 | 8 | 7 | 7 | 272.0 | MF | 20 |
| 7D | 30 | 8 | 4 | 4 | 508.0 | C | 20 |
| 7E | 30 | 8 | 14 | 14 | 124.0 | F | 20 |

TABLE IV-continued

PROCESSING CONDITIONS FOR SAMPLES

| NO. | BERLYN+ RPM | RHEOTEC++ RPM | CASTING ROLL SPEED (RPM) | NIPP ROLL SPEED (RPM) | FILM THICKNESS (microns) | SURFACE* TEXTURE | 1" EXT.' RPM |
|---|---|---|---|---|---|---|---|
| 7F | 30 | 8 | 25 | 25 | 71.0 | VF | 20 |
| 7G | 30 | 8 | 48 | 48 | 25.4 | SF | 20 |

+Berlyn ™ extruder temperature same for all samples: Zone 1 = 149° C., Z2 = 177, Z3 = 193, Z4 = 204, Z5 = 204, Z6 = 204
++Rheotec ™ extruder temperature same for all samples: Zone 1 = 110° C., Z2 = 149, Z3 = 149, Z4 = 160
'1" (2.54 cm) extruder temperature same for all runs: Zone 1 = 143° C., Z2 = 191, Z3 = 191
*F = Fine microtexture, MF = medium fine, VF = very fine, SF = super fine, C = coarse Since the extruder conditions were close to constant for all of the above runs, the core thickness to skin thickness ratio will be the same for all of the above runs, approximately 13:1 as will be the core/tie layer ratio at 30:1. Thus, it will be noted that the total film thickness column of Table IV correlates exactly with the surface texture column. The range of values goes from a total film thickness of 1.0 mil (25 microns) and a texture of super fine, to 20.0 mil (508 microns) and a texture of coarse, all from a stretch of 5:1 and an instantaneous recovery. Thus, it can be seen that the thicker materials give coarser textures and that by controlling the physical parameters, the texture can be controlled.

EXAMPLE 8

A three-layer LLDPE/SIS/LLDPE film was made as in the previous examples using a Berlyn extruder with a screw speed of 20 RPM to feed the Kraton™ 1107, and a Brabender™ extruder with a screw speed of 17 RPM to feed the Dow Chemical 61800 linear low density polyethylene to a Cloeren™ feedblock. The laminate was extruded through a single manifold 18 inch (46 cm) wide film die onto a casting roll at 85° F. (29° C.), and a speed of 13.7 ft/min (4.18 m/min) to give a laminate with a core/skin ratio of 15.6:1 and a total thickness of 125 microns. The film was uniaxially stretched 4:1 and instantaneously recovered, the coefficient of friction of the film to itself was measured for the stretched and recovered film, and compared to the unstretched film. The data is shown in Table V. MD denotes Machine direction and TD denotes transverse direction.

TABLE V

| Sample | Static COF | Dynamic COF |
|---|---|---|
| unstretched MD | 4.5 | 4.2 |
| unstretched TD | 4.6 | 3.7 |
| stretched MD | 0.4 | 0.3 |
| stretched TD | 0.5 | 0.5 |

This data is indicative of the large drop in the coefficient of friction for the stretched film compared to its unstretched precursor and is also indicative of the unique microtextured surface of laminates of the present invention.

EXAMPLE 9

A three-layer laminate of the present invention was made using the set-up of Example 8. The Berlyn™ extruder, operating at a screw speed of 10 RPM, was used to feed a polyurethane (Pellethane™ 2102-75A from Dow Chemical) core material. The Brabender™ extruder operating at a screw speed of 7 RPM was used to feed a blend of Amoco™ (Amoco Oil Co., Chicago, Ill.) 3150B high density polyethylene (HDPE) and Kraton™ 1107 in a 95:5 ratio, as the skin material, to the Cloeren™ feedblock. The small amount of Kraton™ 1107 was added to the skin layer to increase the adhesion of the skin layer to the core layer. The laminate was extruded through a single manifold, 18 inch (46 cm) wide, film die onto a casting roll at a temperature of 70° F. (21° C.) and a speed of 21 ft./min. (6.4 meters/minute) to give a 69 micron laminate with a core/skin ratio of 13.7:1. The laminate exhibited a microtextured surface after stretching 600% and instantaneous recovery.

EXAMPLE 10

A three-layer laminate of the present invention was made using the set up of Example 8. The Berlyn™ extruder operating at a screw speed of 60 RPM was used to feed a triblock copolymer elastomer of styrene-butadiene-styrene (SBS) (Kraton™ 1101) as a core material, and a Killion™ (Killion Extruder Co., Cedar Grove, N.J.) extruder was used to feed a Dow™ 3010 LLDPE material to a Cloeren™ three-layer die. The extrudate was cast upon a casting roll at a temperature of 85° F. (29° C.) and a speed of 41 ft/min (12.5 m/min). The resulting 5 mil (0.127 mm) thick film with a core/skin ratio of 8.9:1 was easily stretched 7.5:1 and upon instantaneous recovery a fine textured laminate was formed.

EXAMPLE 11

A three-layer laminate, of the present invention, made using the set up of Example 4, with the Berlyn™ extruder feeding a Kraton™ G 2703 styrene-ethylene-butylene-styrene (SEBS) block copolymer at a screw speed of 20 RPM, and the Brabender™ extruder feeding an Exxon™ PP-3014 polypropylene at a screw speed of 5 RPM, to a Cloeren™ feedblock. This material was then extruded through a 18 inch (46 cm) film die onto a casting roll at a temperature of 34° F. (1.1° C.). The film produced was easily stretched 600% and formed a fine textured surface after it was allowed to recover instantaneously. The layer thicknesses determined under a light microscope were 15/162/12 microns skin/core/skin, respectively.

EXAMPLE 12

This example demonstrates the use of varying skin and core materials. In all runs, the line conditions were identical using a Cloeren™ feedblock at 400° F. (204° C.). The core extruder was the Brabender™ discussed above with temperatures in zones 1-4 of 178°, 210°, 210° and 216° C. respectively. The die was at 400° F. (204° C.) and the casting wheel at 51° F. (11° C.).

TABLE VI

| # | CORE | SKIN | CORE SKIN RATIO | % STRETCH | SHRINKAGE | TEXTURE |
|---|---|---|---|---|---|---|
| 12A | Kraton™ 1107 | ELVAX™ 360 | 9.6 | 700 | I | F |
| 12B | Kraton™ 1107 | (Polyester) (Chem., Eastabond™ FA-300) | 4.4 | 609 | I | F |

12A in Table VI demonstrates that elastomers can be used for the skin when a more elastic core is used and with appropriate stretch for a 115 micron film. 12B demonstrates the use of a polyester skin in a 120 micron film. The laminate designated 12B, despite the relatively large core-to-skin ratio, was of a relatively fine texture and instant shrink recovery. This is due primarily to the low modulus of the polyester (compare to Example 3). FA-300 is available from Eastman Chem. Co., Kingsport, Tenn.

EXAMPLE 13

Nylon 66 (Vydyne™ 21 of the Monsanto Co., St. Louis, Mo.), the condensation product of adipic acid and hexamethylene diamine, was used as the skin in accordance with the procedure outlined in Example 8. The core was a SIS (Kraton™ 1107) block copolymer. The nylon and Kraton™ were extruded at 525° F. (274° C.) and 450° F. (232° C.), respectively into a 500° F. (260° C.) die. A 4 mil (0.1 mm) thick film was formed with a core to skin ratio of 18:1. A microtextured surface formed after a 4:1 stretch and instant recovery.

EXAMPLE 14

In order to increase the tackiness of the core and lower core layer modulus and decrease its viscosity, a solid tackifying rosin Wingback™ (Goodyear) was blended with Kraton™ 1107 in ratios of 10/90, 20/80 and 30/70 using the arrangement of the previous example, in 91, 114 and 165 micron films, respectively. The die temperature was 380° F. (193° C.) with the Kraton™ blend fed at a rate of 18.5 pounds/hour (0.14 kgs./min.) and the polyethylene skin (LLDPE; Dowlex™ 2500, Dow Chemical) fed at a rate of 6 pounds/hour (2.72 kgs/hr). The core-to-skin ratios were 6.2:1. For all three Kraton™ blends, a fine microtextured surface was obtained when a 6:1 stretch was employed and gave instant shrink recovery.

EXAMPLE 15

The relationship between skin thickness and percent stretch to surface texture (measured by periodicity) was explored using a SEBS core (Kraton™ G1657) and a polypropylene skin (Exxon™ 3085). The Berlyn™ extruder was used for the core, and the Rheotec™ extruder was used for the skin, fed into a Cloeren™ feedblock. A single-layer drop die was used at 420° F. (216° C.), the casting roll operated at 38.9 ft/min (11.9 m/min) and 50° F. (10° C). The results are shown in Table VII below.

TABLE VII

| # | AVG. SKIN THICKNESS (μ) | CORE/ SKIN RATIO | STRETCH % | PERIODI- CITY (μ) | SHRINK MECHAN- ISM |
|---|---|---|---|---|---|
| 15A | 14 | 6 | 600 | 29 | I |
|  |  |  | 250 | 56 | I |
| 15B | 17.5 | 6.1 | 550 | 39 | I |
|  |  |  | 350 |  |  |
| 15C | 21 | 4.4 | 550 | 46 | H |
|  |  |  | 350 | 71 | H |
| 15D | 20 | 4.3 | 550 | 47 | H |
|  |  |  | 300 |  |  |
| 15E | 23 | 3.7 | 500 | 63 | H |
|  |  |  | 350 | 69 | H |

As the stretch percent increased for each sample, the periodicity decreased indicative of the finer microtexturing obtained. This shows that stretch percent can be used to vary the surface structure of the laminate.

Further, as skin thickness increased, so did the periodicity. In all samples, the core thickness was approximately constant at 85 μ's. Skin thickness on a constant core can thus be directly related to the surface texture obtainable. As can be seen in the above Table IV, for relatively constant stretch % as the skin thickness increased so did the periodicity. The thick skinned samples thus produced coarser textures. This can, of course, be used to manipulate the skin and hence laminate characteristics.

EXAMPLE 16

The sample tested was that prepared in Example 8. The stretch ratio was varied from 2:1 to 13:1.

TABLE VIII

| Stretch ratio | Periodicity (μ) | % Area Increase |
|---|---|---|
| 2 | (random wrinkles) |  |
| 3 | 30 |  |
| 4 | 12 |  |
| 5 | 10 | 280 |
| 6 | 8 |  |
| 7 | 7 |  |
| 8 | 6.5 | 390 |
| 9 | 6 |  |
| 10 | 5.5 |  |
| 11 | 5 |  |
| 12 | 4 | 530 |
| 13 | 3 |  |

As can be seen from Table VIII, the relationship between stretch ratio and periodicity demonstrated in Example 15 holds up for this LLDPE/SIS/LLDPE laminate. As the stretch ratio increases, the periodicity decreases first rapidly, then slowly in a substantially exponential manner. Further, the increase in area increases with an increase in stretch ratio.

EXAMPLE 17

The relationship between stretch, core/skin ratio and shrink mechanism was demonstrated using the procedure of Example 4 and Example 15 polypropylene/Kraton™ 1657 (SEBS)/polypropylene laminates. The material was stretched at the rate of 5 cm/sec and held for 15 seconds. The film was allowed to shrink for 20 seconds and then heat shrunk in a water bath for 5 seconds at 160° F. (71.1° C.).

The length of the film after shrink was then compared to the length of the film after the 20 second hold period and the length after stretch to determine the shrink mechanism in operation. The results of this comparison is shown in FIG. 10, and in Table IX below.

TABLE IX

| CORE/SKIN RATIO | STRETCH RATIO(S) | SHRINK MECHANISM |
| --- | --- | --- |
| 6.0 | 3.8/5.3/6.2 | I |
| 5.3 | 4.6/5.3 | S |
|  | 6.5 | I |
| 5.1 | 4.3/5.0 | H |
|  | 5.5 | S |
|  | 6.8 | I |
| 4.8 | 4.2/4.0 | H |
|  | 6.0 | T |
|  | 6.5 | F |
| 4.0 | 4.0/5.2/6.0 | H |
| 3.7 | 4.2–6.8 | H |
| 3.4 | 4.0 | N |
|  | 4.7–6.0 | H |

N = None, H = Heat, S = Slow time, T = Time, F = Fast time, I = Instant

Fast is when more than 15% recovery occurred at seconds. Medium time is where greater than 15% recovery occurred at 20 seconds. Slow time is where greater than recovery was not noted until 60 seconds after stretch.

EXAMPLE 18

Polypropylene (Exxon™ 3145) was added to a Kraton™ 1107 (SIS) elastomer as a modifier for the core material. The skin used was an Exxon™ 3014 polypropylene (PP). The cores prepared contained 5 and 10 percent Exxon™ 3145 polypropylene by weight. The relationship between stretch, the shrink mechanism and texture was tested. The results are in the following Table.

TABLE X

| Core/Skin Ratio = 6.9, 112 microns thick, 10% PP in Core | | | | |
| --- | --- | --- | --- | --- |
| % Stretch | 320 | 410 | 510 | 590 |
| Shrink Mechanism | None | None | Heat | Heat |
| Texture | — | — | Coarse | Coarse |
| Core/Skin Ratio = 8.0, 125 microns thick, 10% PP in Core | | | | |
| % Stretch | 280 | 380 | 480 | 570 |
| Shrink Mechanism | None | None | Heat | Heat |
| Texture | — | — | Coarse | Coarse |

| Core/Skin Ratio = 8.8, 84 microns thick, 5% PP in Core | | | | | |
| --- | --- | --- | --- | --- | --- |
| % Stretch | 270 | 320 | 400 | 500 | 590 |
| Shrink Mechanism | Heat | Heat | Heat | Slow Time | Fast Time |
| Texture | Coarse | Coarse | Coarse | Med | Fine |

As can be seen, the addition of PP to the core decreases the shrinkability of the laminate. The polypropylene appears to reduce the elasticity of the core thereby permitting the restraining forces of the skin to more easily dominate the elastic strain imposed by the deformed elastic core.

EXAMPLE 19

Figure 11:
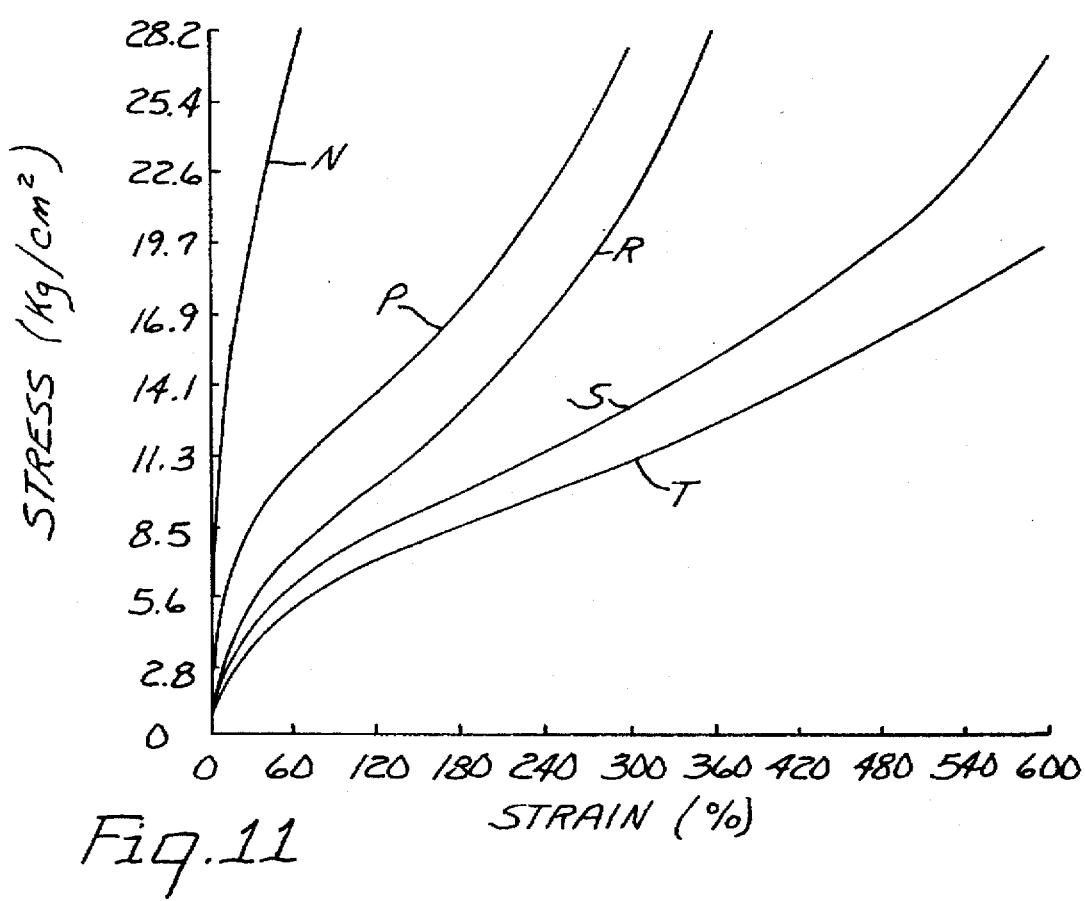
FIG. 11 (T–N) are stress/strain curves for a series of laminate films.

The effect of adding a stiffening aid, polystyrene, to an elastomeric core material was tested. The skin comprised a linear low density polyethylene (Dowlex™ 6806). The core was a blend of SIS (Kraton™ 1107) and polystyrene (500PI or 685W, both from Dow Chemical Co.). All samples were of a three-layer construction (skin/core/skin) with a total thickness of 4.5 mil (0.11 mm) and a core/skin ratio of 8:1. All samples were then stretched 400% and instantaneously recovered. Tensile curves were then generated which demonstrated that the laminates became stiffer with increasing polystyrene content (as shown in FIG. 11 (T–N), shown also in the following Table XI).

TABLE XI

| SAMPLE # | % P.S. (Type) | 5% YOUNGS MODULUS (kg/cm$_2$) |
| --- | --- | --- |
| 19A(T) | 0 | 11.5 |
| 19B(S) | 10 (500 PI) | 20.7 |
| 19C(R) | 30 (500 PI) | 29.4 |
| 19D(P) | 40 (685 W) | 68.6 |
| 19E(N) | 50 (685 W) | 188.4 |

EXAMPLE 20

In this example, the effect of the addition of Wingtack™ tackifier to the, core elastomer was investigated. The laminate material of Example 14 was compared to a 3 layer laminate (20) comprising LLDpE/Kraton™ 1107/LLDPE. Both samples were 4 mil (0.10 mm) in total thickness with core/skin ratios of approximately 8:1. These materials were of the instant shrink type when stretched from 4:1 to 13:1.

TABLE XII

| EXAMPLE | 5% YOUNGS MODULUS |
| --- | --- |
| 20 (Comp) | 109 kg/cm$^2$ |
| 14 | 47.9 kg/cm$^2$ |

As can be seen from Table XII, the use of a viscosity reducing aid/tackifier has the opposite affect as the addition of a polystyrene stiffening aid.

EXAMPLE 21

A two-layer laminate of a core and one skin layer was formed of Kraton™ 1107 (S.I.S.)/Exxon™ polypropylene 3014. A Berlyn™ extruder operating at 6 RPM was used with the polypropylene and a Killion™ extruder operating at 125 RPM was used for the Kraton™. The polymers were fed to an 18 inch (45.7 cm) 440° F. (227° C.) Cloeren™ die with one manifold shut down. The resulting film was cast on a roll at 60° C. and rotating at 35.2 RPM. The laminate formed was 2 mil (0.051 mm) thick with a core/skin ratio of 2.5:1 and exhibited a coarse microtexture when stretched 5:1 and allowed to recover instantly. Necking on subsequent restretching was only 2.5%.

EXAMPLE 22

A laminate was formed having skins of different compositions. The elastic core was Kraton™ 1107 with one polyethylene (Dow™ LLDPE 61800) and one polypropylene (Exxon™ 3085) skin. The core was extruded with Berlyn™ extruder while the skins were extruded with a Rheotec™ and Brabender™ extruders, respectively. The Cloeren™ die was at 350° F. (177° C.) and the casting roll at 60° F. (16° C.).

Two films were formed. For the first, the extruders operated at 20, 8 and 26 RMP's respectively while the cast roll operated at 17.3 RPM to form laminates with core/skin ratios of 18:1. The sample formed was instant shrink at a 5:1 stretch, with a fine microtexture. For the second film, the extruders and cast roll operated at 10, 16, 26 and 14.2 RMP's respectively to form a laminate with a core/skin ratio of 18:1. The second laminate was also instant shrink at 5:1 stretch yet exhibited coarse surface texture. Both laminated were 4.0 mil (0.1 mm) thick.

EXAMPLE 23

The laminate of Example 16 was stretched in a first direction by 8:1 and sequentially in a cross direction by 4:1. This laminate was of the instant shrink type. The texture formed is shown in FIG. 15.

EXAMPLE 24

The laminate of Example 3A was stretched in a first direction at 4:1 and sequentially in a cross direction by 4:1. This laminate was of the instant shrink type. The texture formed is shown in FIG. 16.

EXAMPLE 25

The laminate of 3A was stretched simultaneously biaxially at 4:1 by 4:1. The laminate recovered instantly. The core/skin thickness of unstretched laminate was 90/5 microns, respectively.

EXAMPLE 26

A three-layer laminate of polypropylene/SEBS(Kraton™ 1657)/polypropylene used in Example 17 was tested for writability. The core/skin ratio was 5:1 with a total laminate thickness of 5 mil (0.13 mm). The film was stretched to 5:1 and allowed to recover. The writability before and after stretching is shown in FIGS. 8 and 9 respectively.

EXAMPLE 27

A series of LLDPE/SIS/LLDPE laminates were compared for their non-necking characteristics, as shown in Table XIII below.

TABLE XIII

| # | C/S RATIO | STRETCH RATIO | THICKNESS (microns) | % WIDTH CHANGE |
| --- | --- | --- | --- | --- |
| A | 8.75 | 5:1 | 215 | 2.8 |
| B | 6.0 | 5:1 | 120 | 3.2 |
| C | 6.7 | 5:1 | 78 | 5.2 |
| D | 15.3 | 7:1 | 100 | 10.0 |
| E | 21.2 | 8:1 | 132 | 33.3 |
| F | PURE SIS | 5:1 | | 50.0 |
| G | " | 7:1 | | 62.5 |
| H | " | 8:1 | | 70.8 |

The first 3 examples are from Example 2, and SIS was also tested for comparison purposes. As the C/S ratio and stretch ratios rose the problems with necking increased.

EXAMPLE 28

The use of adhesive cores was demonstrated. First a copolymer of isooctyl acrylate (IOA) and acrylic acid (AA) in monomer ratios of (90/10) was used as a core with polypropylene (Exxon™ 3014) and PET (intrinsic viscosity 0.62) as the skins in the first two examples. The IOA/AA copolymer was prepared in accordance with U.S. Pat. No. 4,181,752. The core/skin ratios and total thicknesses were 20 and 10, and 22 mil (0.56 mm) and 6 mil (0.15 mm) before lamination for the PP and PET examples, respectively. The laminates were cured for 5 minutes using a 15 watt UV light to cure the cores. The PP skin embodiment was an instant shrink at 500% stretch while the PET skin embodiment was a heat shrink laminate at 400% stretch.

PET was also used as a skin layer for a Kraton™ 1107 (56 parts) Wingtack Plus™ (35 parts) and Wingtack™ 10 (9 parts) core with a core/skin ratio of 83:1 and a total thickness of 25.6 mil (0.65 mm) before lamination. This laminate was of the instant shrink type at 400% stretch.

EXAMPLE 29

This example demonstrates skin controlled relaxation in the heat shrink region and control of the heat shrink mechanism by % elongation and core/skin ratio. A series of 5 mil(0.12 mm) laminates were made with a core of Kraton™ 1107 (89 parts) poly(alpha-methyl)styrene (10 parts) and Irganox™ (Ciba-Geigy Corp., Hawthorne, N.Y.)) (1 part-antioxidant). The skins were polypropylene (Exxon™ 3085). A Berlyn™ extruder was used for the core and Rheotec™ extruders for the skin using a Cloeren™ 3 layer feedblock and a 18 inches (45.7 cm) film die. The cast wheel temperature was 80° F. (27° C.) with the speed determined by the core/skin (C/S) ratio and the skin extruder speed. The shrink mechanism as a function of C/S ratio and % stretch is shown in FIG. 20. Fast is when more than 15% recovery occurred at 5 seconds. Medium time is where greater than 15% recovery occurred at 20 seconds. Slow time is where greater than 15% recovery was not noted until 60 seconds after stretch.

Figure 21:
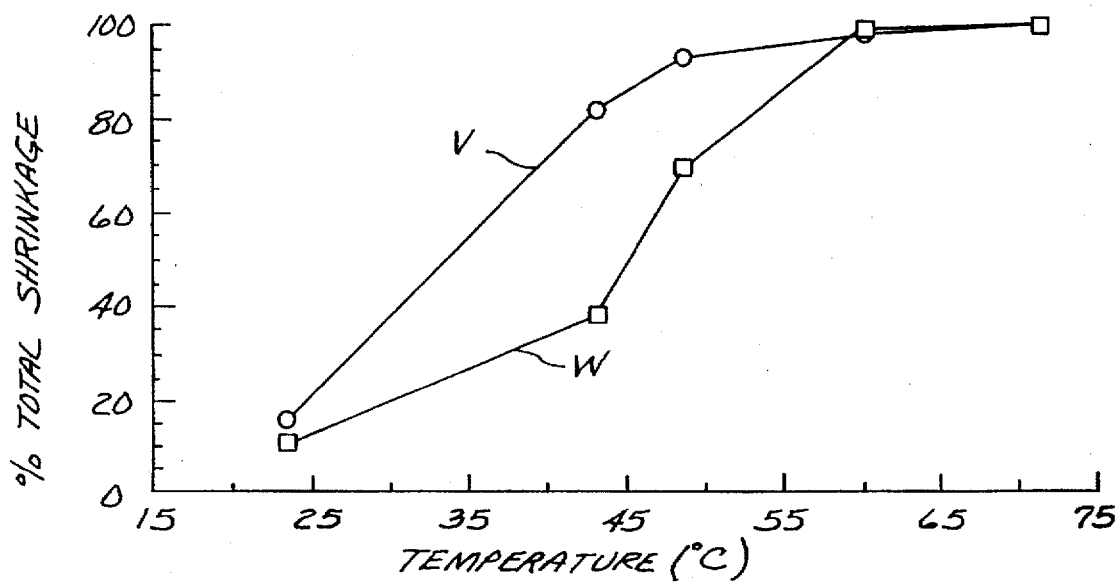
FIG. 21 is a diagram showing the relationship between the core/skin ratio, the percent of total recovery and activation temperature.

Skin control of the temperature of activation for the heat shrink material is demonstrated in FIG. 21. The temperature of activation is defined as the temperature required to achieve 50% or 90% of the recovery obtainable. Lines V and W represent samples with core/skin ratios of 4.71 and 4.11, respectively. As is seen, as the core/skin ratio went down the temperature of activation (both $T_{a-90}$ and $T_{a-50}$) went up, indicating a skin controlled relaxation. In this Figure, the 100% value is defined as the % shrinkage at 160° F. (71° C.), which for most practical purposes was the upper limit of available recovery. The points below 80° F. (27° C.) are the amounts of preactivation shrinkage for each example.

Three samples were also tested for the increase opacity from the unstretched clear film as seen in Table XIV below.

TABLE XIV

| CORE*/SKIN RATIO | % STRETCH | TEXTURE | SHRINK MECHANISM | OPACITY AS CAST | OPACITY ACTIVATED |
| --- | --- | --- | --- | --- | --- |
| 4.71 | 300 | C | H | 2.42% | 30.4% |
| 4.97 | 700 | F | I | 2.08 | 37.5 |
| 5.0 | 300 | C | H | 3.40 | 35.8 |

*The core had a ½% blue pigment.

EXAMPLE 30

A foamed core three-layer film was made. The skins were Dow™ LLDPE 6806 and the core was 99.5% Kraton™ 1107 with 0.5% AZNP 130 blowing agent (Uniroyal Chemical Co., Naugatuck, Conn). Total film thickness was 20 mil (0.5 mm). The skins were 2.0 mil (0.05 mm) thick each. The foamed core specific gravity was 0.65 as compared to unfoamed Kraton™ specific gravity of 0.92. A three layer coextrusion die was used. This was an instant shrink sheet exhibiting a coarse texture at about 300% stretch.

EXAMPLE 31

The film from Example 2 with a core/skin ratio of 6:1 was characterized for its unstretched and stretched modulus value, the results of which are shown in FIG. 5; X is the Kraton™ 1107 elastomer alone, ZZ is the polyethylene skin alone, Z is the laminate as cast and Y is the laminate after stretching to 500% and recovery.

EXAMPLE 32

The film laminate of certain examples were examined to determined the contact mechanism between the skin and core layers. The stretched and activated samples were cut with a razor blade on a hard surface. The samples were then examined at the cut edges with a scanning electron microscope. The core/skin contact was then determined visually with the results summarized in Table XV below.

TABLE XV

| Ex | Composition | Stretch Ratio | Comments |
|---|---|---|---|
| 5 | PVDF + PMMA/SIS/PVDF + PMMA | 2.2 | Elastic cohesive failure |
| 6 | PB/SIS/PB | 3 | Elastic cohesive failure |
| 7 | PE/EVA/SIS/EVA/PE | 5 | Adhesive failure |
| 12A | EVA/SIS/EVA | 4 | Adhesive failure |
| 12C | FA300/SIS/FA300 | 7 | Adhesive failure |
| 19E | PE/SIS + PS/PE | 3 | Some voids |
| 8 | LLDPE/SIS/LLDPE | 3 | Filled |
|  |  | 5 | Filled |
|  |  | 7 | Filled |
| 15A | PP/SEBS/PP | 4 | Filled |
| 15C | PP/SEBS/PP | 5.3 | Elastic cohesive failure |
| A | PP/SIS/PP | 5.0 | Filled |

New sample A corresponds to Example 29. Sample A had approximately the caliper of the Example 29 samples with a core/skin ratio of 5.1 and was a heat shrink laminate. Example 12C corresponds to the scanning electron micrograph designated FIG. 24. Example 32A is shown in FIG. 22. Example 6 corresponds to FIG. 23.

EXAMPLE 33

A sample having the layer composition of Example 29 (with 1% blue pigment in the core) was formed with an overall caliper of 3.0 mils (0.076 mm) and a core/skin ratio of 5.14. The film was cast onto a chrome casting wheel with a rubber nip. The 60° gloss was measured using ASTM D2457-70 using a Gardner Instruments(Bethesda, Md.) 60° gloss tester. The results are summarized in Table XVI below for the as cast and three microtextured films (with different stretch rates).

TABLE XVI

|  |  | 60° C. Gloss | |
|---|---|---|---|
|  |  | MD | TD |
| As Cast | Chrome Side | 8.6 | 8.8 |
|  | Rubber Side | 3.4 | 3.3 |
| 300% | Chrome Side | 2.1 | 3.5 |
|  | Rubber Side | 1.5 | 1.9 |
| 400% | Chrome Side | 2.0 | 6.6 |
|  | Rubber Side | 1.6 | 2.4 |
| 500% | Chrome Side | 2.2 | 3.0 |
|  | Rubber Side | 1.6 | 1.8 |

Comparative Example 1

Figure 19:
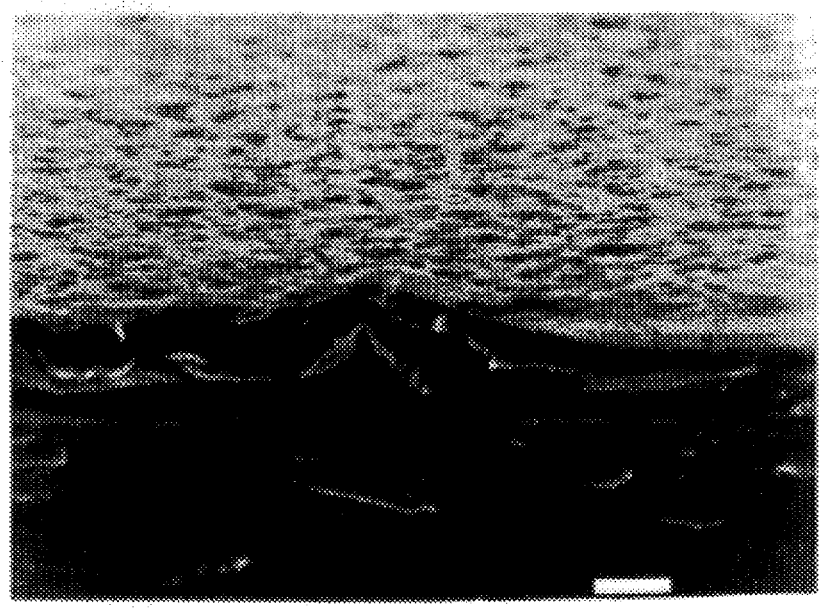
FIG. 19 is a scanning electron micrograph (100×) of a non-textured laminate prepared by a prior art method.

A three-layer film of Dow™ LLDPE 2517 (Polyethylene) /Pebax™ (Autochem, France) 3533/LLDPE 2417 was made. The film was formed by pressing three precursor films together at 400° F. (20° C.) and about 2000 pounds of pressure (140 kg/sq.cm) for 5 minutes. The film formed was 5 mil (0.13 mm) thick with a core/skin ratio of 12.7. The laminate was stretched 400% (from 1 to 5 cm). The stretched laminate then contracted to 3.2 cm (36% of stretched length) at room temperature. The relaxed laminate was then heat shrunk by 180° F. (82° C.) air and it contracted to 1.5 cm (53% of relaxed length). An edge of the sample was then cut and observed for microtexturing. No folds were observed at 1000× magnification. Microscopic bumps, probably formed by recompression of the cover layer, and skin delamination was observed, see FIG. 19. The C.O.F. and opacity for the cast laminate was 0.901 and 2.77% while that for the relaxed activated laminate was 0.831 and 12.4%, respectively.

The various modifications and alterations of this invention will be apparent to those skilled in the art without departing from the scope and spirit of this invention and this invention should not be restricted to that set forth herein for illustrative purposes.

We claim:

1. An elastomeric laminate consisting essentially of at least one elastomeric layer and at least one continuous microtextured skin layer over substantially the entire laminate wherein:
    (a) the microtexture on said skin layer is formed by stretching an untextured laminate past the deformation limit of at least one untextured skin layer and allowing the stretched laminate to elastically recover over the entire region stretched and
    (b) said at least one elastomeric layer and said at least one continuous microtextured skin layer are in substantially continuous contact.

2. The elastomeric laminate of claim 1 wherein the microtexture comprises folding of said at least one continuous microtextured skin layer.

3. The elastomeric laminate of claim 1 wherein the coefficient of friction of said at least one continuous microtextured skin layer is less than 50% of the coefficient of friction of a corresponding non-textured laminate.

4. The elastomeric laminate of claim 1 wherein said at least one continuous microtextured skin layer is an inner layer.

5. The elastomeric laminate of claim 1 wherein said at least one continuous microtextured skin layer is an outer layer.

6. The elastomeric laminate of claim 1 wherein the deformation of said at least one continuous microtextured skin layer is created by uniaxial stretching.

7. The elastomeric laminate of claim 1 wherein the deformation of said at least one continuous microtextured skin layer is created by simultaneous biaxial stretching.

8. The elastomeric laminate of claim 1 wherein the deformation of said at least one continous microtextured skin layer is created by sequential biaxial stretching.

9. A colored elastomeric ribbon comprising at least one layer having an added colorant and at least one opaque polymeric skin layer, wherein said at least one opaque polymeric skin layer is a microtextured outer layer.

10. The colored elastomeric ribbon of claim 9 wherein said at least one layer having an added colorant is an elastomeric core layer.

11. The colored elastomeric laminate of claim 9 wherein the laminate microtexture is formed by multiaxially stretching of the laminate.

12. A sheet laminate comprising at least one elastomeric layer and at least one outer microtextured skin layer wherein:

(a) the sheet has enclosed or partially enclosed spaces for entrapping dust or oil and (b) the laminate microtexture is formed by multiaxially stretching the laminate.

13. The sheet laminate of claim 12 wherein the laminate is sequentially biaxially stretched.

14. The sheet laminate of claim 12 comprising a dust mat wherein the laminate is simultaneously biaxially stretched.

* * * * *